(12) United States Patent
Cook et al.

(10) Patent No.: US 10,557,754 B2
(45) Date of Patent: Feb. 11, 2020

(54) SPECTROMETRY IN INTEGRATED CIRCUIT USING A PHOTONIC BANDGAP STRUCTURE

(71) Applicant: Texas Instruments Incorporated, Dallas, TX (US)

(72) Inventors: Benjamin Stassen Cook, Addison, TX (US); Daniel Lee Revier, Addison, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/800,009

(22) Filed: Oct. 31, 2017

(65) Prior Publication Data

US 2019/0128735 A1    May 2, 2019

(51) Int. Cl.
| | | |
|---|---|---|
| H01L 21/00 | (2006.01) | |
| G01J 3/02 | (2006.01) | |
| G02B 6/122 | (2006.01) | |
| G01N 21/3581 | (2014.01) | |
| G01J 3/12 | (2006.01) | |

(52) U.S. Cl.
CPC .......... *G01J 3/0259* (2013.01); *G01J 3/0208* (2013.01); *G01J 3/12* (2013.01); *G01N 21/3581* (2013.01); *G02B 6/1225* (2013.01)

(58) Field of Classification Search
CPC .. G01M 21/3581; G02B 6/122; G01J 3/0259; G01J 3/0208; G01J 3/12
See application file for complete search history.

(56) References Cited

U.S. PATENT DOCUMENTS

| | | |
|---|---|---|
| 3,868,759 A | 3/1975 | Hartleroad et al. |
| 3,868,764 A | 3/1975 | Hartleroad et al. |
| 4,974,590 A | 12/1990 | Saito |
| 4,999,587 A | 3/1991 | Evans |
| 5,355,577 A | 10/1994 | Cohn |

(Continued)

FOREIGN PATENT DOCUMENTS

| | | |
|---|---|---|
| SU | 1780469 A1 | 10/1995 |
| WO | 2006101577 A2 | 9/2006 |
| WO | 2017111892 A1 | 6/2017 |

OTHER PUBLICATIONS

"Opticial Sensor-On-Chip ICs Simplify Handheld Spectrometer Design", available at https://www.digikey.com/en/articles/techzone/2017/jun/optical-sensor-on-chip-ics-simplify-handheld-spectrometer-design, Digi-Key Electronics, Jun. 28, 2017, pp. 1-6.

(Continued)

*Primary Examiner* — Richard A Booth
(74) *Attorney, Agent, or Firm* — Michael A. Davis, Jr.; Charles A. Brill; Frank D. Cimino

(57) ABSTRACT

An encapsulated package is provided that includes an integrated circuit (IC) die. An encapsulation material encapsulates the IC die. A set of broadband spectral sensors on the IC die are configured to generate a set of signals in response to electromagnetic energy received by the spectral sensors. A photonic filter structure within the encapsulation material is positioned adjacent the set of spectral sensors. The photonic filter structure is configured to pass a different frequency band of electromagnetic energy to each of the set of spectral sensors.

18 Claims, 14 Drawing Sheets

(56) References Cited

U.S. PATENT DOCUMENTS

| | | | | |
|---|---|---|---|---|
| 5,500,912 A | * | 3/1996 | Alonas | G02B 6/4295 257/E31.108 |
| 5,528,074 A | | 6/1996 | Goto et al. | |
| 5,834,320 A | | 11/1998 | Huddleston et al. | |
| 6,664,615 B1 | | 12/2003 | Bayan et al. | |
| 6,967,347 B2 | * | 11/2005 | Estes | B82Y 10/00 257/25 |
| 6,979,105 B2 | | 12/2005 | Leysath | |
| 7,228,016 B2 | | 6/2007 | Beausoleil | |
| 7,305,161 B2 | | 12/2007 | Zhou | |
| 7,733,198 B1 | | 6/2010 | Olsson et al. | |
| 8,031,012 B2 | | 10/2011 | Hasegawa | |
| 8,054,145 B2 | | 11/2011 | Mohammadi et al. | |
| 8,094,023 B1 | | 1/2012 | El-Kady et al. | |
| 8,138,868 B2 | | 3/2012 | Arnold | |
| 8,143,637 B2 | | 3/2012 | Kanatake | |
| 8,587,182 B2 | | 11/2013 | Reiche | |
| 9,018,074 B2 | | 4/2015 | Zhang et al. | |
| 9,070,703 B2 | * | 6/2015 | Haroun | H01L 23/66 |
| 9,123,737 B2 | | 9/2015 | Haroun et al. | |
| 9,343,426 B1 | | 5/2016 | Parvarandeh | |
| 9,373,878 B2 | | 6/2016 | Schuppener et al. | |
| 9,450,563 B2 | | 8/2016 | Gorisse et al. | |
| 9,583,811 B2 | | 2/2017 | Seler et al. | |
| 9,647,329 B2 | | 5/2017 | Herbsommer et al. | |
| 9,651,718 B2 | | 5/2017 | Chen et al. | |
| 10,062,583 B2 | | 8/2018 | Costa et al. | |
| 10,139,564 B1 | | 11/2018 | Homeijer et al. | |
| 2005/0224956 A1 | | 10/2005 | Kao et al. | |
| 2006/0038168 A1 | | 2/2006 | Estes et al. | |
| 2006/0054780 A1 | | 3/2006 | Garrood et al. | |
| 2007/0108545 A1 | * | 5/2007 | Chua | H01L 27/1462 257/433 |
| 2008/0112665 A1 | | 5/2008 | Beausoleil et al. | |
| 2008/0218299 A1 | | 9/2008 | Arnold | |
| 2009/0288852 A1 | | 11/2009 | Hirokawa et al. | |
| 2010/0019247 A1 | | 1/2010 | Joichi et al. | |
| 2011/0001233 A1 | | 1/2011 | Iwase et al. | |
| 2011/0089815 A1 | | 4/2011 | Yeh et al. | |
| 2011/0103632 A1 | | 5/2011 | Leclair et al. | |
| 2011/0133597 A1 | | 6/2011 | Pavlov et al. | |
| 2011/0221057 A1 | | 9/2011 | Lin et al. | |
| 2012/0043628 A1 | | 2/2012 | Martin et al. | |
| 2012/0098611 A1 | | 4/2012 | Sinha et al. | |
| 2012/0154168 A1 | | 6/2012 | Duncan et al. | |
| 2013/0038174 A1 | | 2/2013 | Kim et al. | |
| 2013/0228796 A1 | | 9/2013 | Mieczkowski | |
| 2014/0287703 A1 | | 9/2014 | Herbsommer et al. | |
| 2014/0326902 A1 | | 11/2014 | Tehan et al. | |
| 2015/0237423 A1 | | 8/2015 | Bahr et al. | |
| 2015/0295305 A1 | | 10/2015 | Herbsommer et al. | |
| 2016/0028367 A1 | | 1/2016 | Shealy | |
| 2016/0276311 A1 | | 9/2016 | Meyer et al. | |
| 2016/0327977 A1 | | 11/2016 | Tang et al. | |
| 2017/0084519 A1 | | 3/2017 | Speight et al. | |
| 2017/0108655 A1 | | 4/2017 | Zarbock et al. | |
| 2017/0186793 A1 | * | 6/2017 | Ockenfuss | H01L 27/1462 |
| 2017/0253476 A1 | | 9/2017 | Shibuya et al. | |
| 2017/0276870 A1 | | 9/2017 | Snyman | |
| 2017/0288123 A1 | | 10/2017 | Hatano et al. | |
| 2017/0292884 A1 | | 10/2017 | Ching, Jr. et al. | |

OTHER PUBLICATIONS

"Phonon", Wikipedia, available at https://en.wikipedia.org/wiki/Phonon on Aug. 2, 2017, pp. 1-9.

Yan Pennec and Bahram Djafari-Rouhani, "Fundamental Properties of Phononic Crystal", Chapter 2 in "Phononic Crystals", 2016, pp. 23-50.

Daniel Frederic Sievenpiper, "High-Impedance Electromagnetic Surfaces", 1999, University of California, pp. 1-162.

"7 Families of Additive Manufacturing", According to ASTM F2792 Standards, Hybrid Manufacturing Technologies, pp. 1-2.

"Standard Terminology for Additive Manufacturing Technologies", ASTM International, F2792-12a,Sep. 9, 2013, pp. 1-3.

Nagi Elabbasi, "Modeling Phononic Band Gap Materials and Structures", Comsol Blog, Feb. 10, 2016, pp. 1-7.

Dr. Qin Hu, "Multiphoton Lithograpy Based 3D Micro/Nano Printing", EPSRC Centre for Innovative Manufacturing in Additive Manufacturing, pp. 1-30.

Hideo Kosaka et al, "Self-Collimating Phenomena in Photonic Crystals", Applied Physics Letters, vol. 74, No. 9, Mar. 1, 1999, pp. 1212-1214.

Benjamin Stassen Cook and Daniel Lee Revier, "Thermal Management in Integrated Circuit Using Phononic Bandgap Structure", U.S. Appl. No. 15/92,580, filed Oct. 24, 2017, pp. 1-33.

Benjamin Stassen Cook and Daniel Lee Revier, "Electromagnetic Interference Shield within Integrated Circuit Encapsulation Using Photonic Bandgap Structure", U.S. Appl. No. 15/799,757, filed Oct. 31, 2017, pp. 1-38.

Benjamin Stassen Cook and Daniel Lee Revier, "integrated Circuit with Dielectric Waveguide Connector Using Photonic Bandgap Structure", U.S. Appl. No. 15/800,042, filed Oct. 31, 2017, pp. 1-42.

Benjamin Stassen Cook and Daniel Lee Revier, "Galvanic Signal Path Isolation in an Encapsulated Package Using a Photonic Structure", U.S. Appl. No. 15/799,140, filed Oct. 31, 2017, pp. 1-38.

Daniel Lee Revier and Benjamin Stassen Cook, "Acoustic Management in Integrated Circuit Using Phononic Bandgap Structure", U.S. Appl. No. 15/792,591, filed Oct. 24, 2017, pp. 1-37.

International Search Report for PCT/US2018/049166 dated Dec. 13, 2018.

International Search Report for PCT/US2018/049135 dated Dec. 13, 2018.

International Search Report for PCT/US2018/058478 dated Feb. 14, 2019.

Mohammadi, et al. Complete phononic bandgaps and bandgap maps in two-dimensional silicon phononic crystal plates; Electronics Letters Aug. 2, 2017, vol. 43 No. 16. 2 pages.

International Search Report for PCT/US2018/058481 dated Feb. 7, 2019.

International Search Report for PCT/US2018/058487 dated Feb. 14, 2019.

International Search Report for PCT/US2018/057358 dated Feb. 7, 2019.

International Search Report for PCT/US2018/057351 dated Feb. 7, 2019.

International Search Report for PCT/US2018/058494 dated Feb. 21, 2019.

\* cited by examiner

SPECTROMETRY IN INTEGRATED CIRCUIT USING A PHOTONIC BANDGAP STRUCTURE

FIELD OF THE DISCLOSURE

This disclosure relates to an integrated circuit package that includes a photonic bandgap structure in the package encapsulation material.

BACKGROUND OF THE DISCLOSURE

Individual discrete components are typically fabricated on a silicon wafer before being cut into separate semiconductor die and assembled in a package. The package provides protection against impact and corrosion, holds the contact pins or leads which are used to connect from external circuits to the device, and dissipates heat produced in the device.

Wire bonds may be used to make electrical connections between an integrated circuit and the leads of the package with fine wires connected from the package leads and bonded to conductive pads on the semiconductor die. The leads external to the package may be soldered to a printed circuit board. Modern surface mount devices eliminate the need for drilled holes through circuit boards and have short metal leads or pads on the package that can be secured by reflow soldering.

Many devices are encapsulated with an epoxy plastic that provides adequate protection of the semiconductor devices and mechanical strength to support the leads and handling of the package. Some integrated circuits have no-lead packages such as quad-flat no-leads (QFN) and dual-flat no-leads (DFN) devices that physically and electrically couple integrated circuits to printed circuit boards. Flat no-lead devices, also known as micro leadframe (MLF) and small outline no-leads (SON) devices, are based on a surface-mount technology that connects integrated circuits to the surfaces of printed circuit boards without through-holes in the printed circuit boards. Perimeter lands on the package provide electrical coupling to the printed circuit board.

A dielectric is an electrical insulator that can be polarized by an applied electric field. When a dielectric is placed in an electric field, electric charges do not flow through the material as they do in a conductor, but only slightly shift from their average equilibrium positions causing dielectric polarization. Because of dielectric polarization, positive charges are displaced toward the field and negative charges shift in the opposite direction. This creates an internal electric field which reduces the overall field within the dielectric itself. If a dielectric is composed of weakly bonded molecules, those molecules not only become polarized, but also reorient so that their symmetry axis aligns to the field. While the term "insulator" implies low electrical conduction, "dielectric" is typically used to describe materials with a high polarizability which is expressed by a number called the relative permittivity ($\varepsilon r$). The term insulator is generally used to indicate electrical obstruction while the term dielectric is used to indicate the energy storing capacity of the material by means of polarization.

Permittivity is a material property that expresses the force between two point charges in the material. Relative permittivity is the factor by which the electric field between the charges is decreased or increased relative to vacuum. Relative permittivity is also commonly known as dielectric constant.

BRIEF DESCRIPTION OF THE DRAWINGS

Particular embodiments in accordance with the disclosure will now be described, by way of example only, and with reference to the accompanying drawings.

Figure 1:
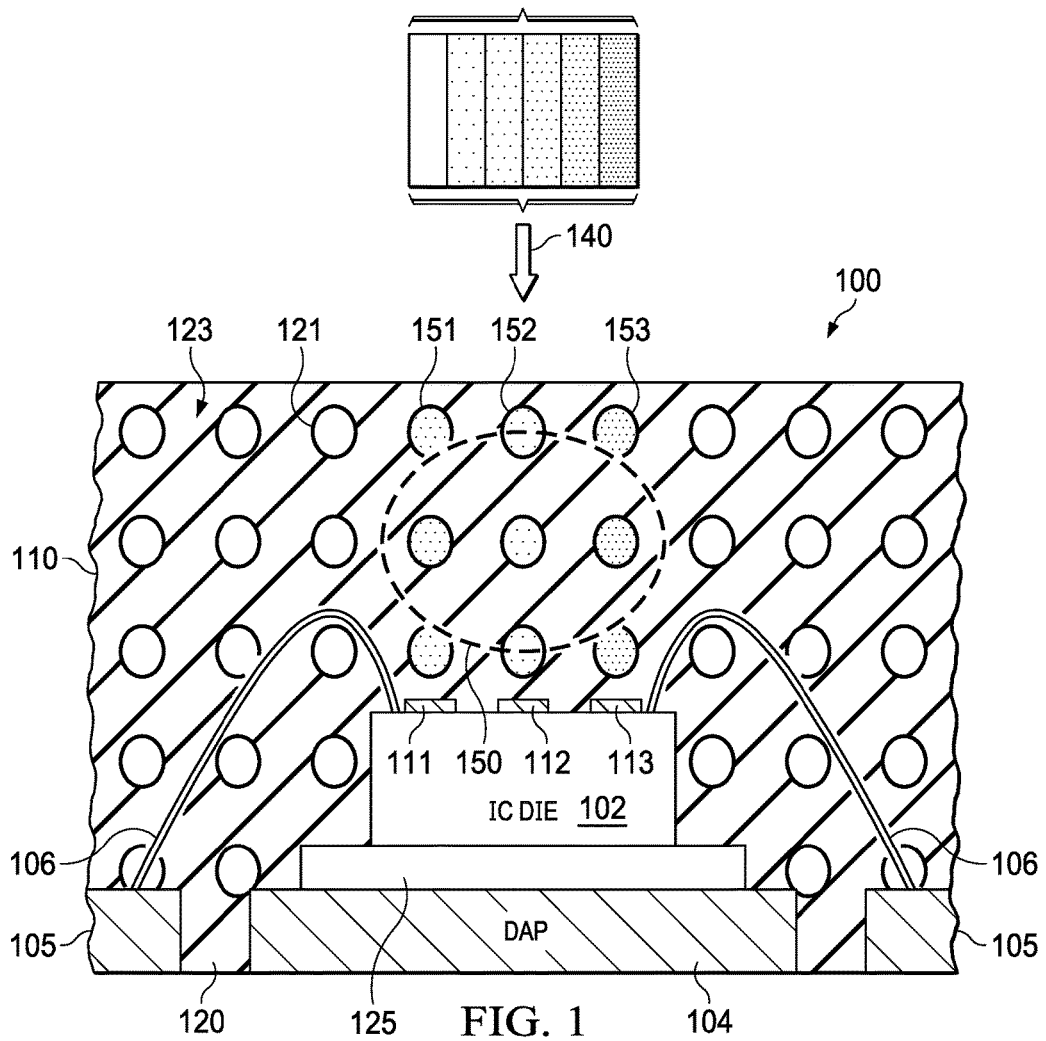
FIG. 1 is an example integrated circuit (IC) package that includes photonic filter structure formed by a photonic collimating structure.

Other features of the present embodiments will be apparent from the accompanying drawings and from the detailed description that follows.

DETAILED DESCRIPTION OF EMBODIMENTS OF THE DISCLOSURE

Specific embodiments of the disclosure will now be described in detail with reference to the accompanying figures. Like elements in the various figures are denoted by like reference numerals for consistency. In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

The epoxy encapsulant for semiconductor chips/packages has typically served the primary purpose of providing environmental and mechanical protection for the integrated circuit (IC). Previously, in order for an additional package function to be added, it must be added before or after the encapsulation step. Performing additional packaging steps may increase cost and limit functionality on the processes that can be performed. A method for encapsulating an IC will now be disclosed in which a structure to perform an additional package function may be created during the process of encapsulation.

A spectrometer is a scientific instrument originally used to split light into an array of separate colors, called a spectrum. Spectrometers were developed in early studies of physics, astronomy, and chemistry. The capability of spectroscopy to determine chemical composition drove its advancement and continues to be one of its primary uses.

In physics, a photon represents an energy packet, or "quanta" of electromagnetic waves. A photon is massless, has no electric charge, and is a stable particle. In the momentum representation of the photon, a photon may be described by its wave vector which determines its wavelength and direction of propagation.

Prior spectrometry sensors require open packaging to allow photons to be able to strike the sensor surface. This leaves the delicate sensor open to the environment or at least more easily accessible. The sensor may be discrete from the processing IC in many implementations.

Additive manufacturing has enabled the deposition of patterned materials in a rapid and cost efficient manner. By utilizing additive manufacturing, control structures may be integrated directly into the encapsulation material of an IC. As will be disclosed herein, a spectrometer sensor may be fabricated on an IC die that is included within an encapsulated package. A filter structure may be provided by the implementation of multi-material photonic bandgap (PBG) structures within the encapsulation material to allow sensing of a selected frequency band of photon energy that falls on the encapsulated package.

FIG. 1 is an example encapsulated integrated circuit (IC) package 100 that includes a filter structure formed by a photonic collimating structure 150 within the encapsulant material 120. As will be described in more detail below, filter structure 150 may be configured to selectively filter frequency bands from electromagnetic energy that falls on a surface of encapsulated package 102. For example, filter region 151 may allow a first band of energy to pass, filter region 152 may allow a second band of energy to pass, and filter region 153 may allow a third band of energy to pass. One or more sensors fabricated on IC die 102, such as sensors 111-113, may then sense the energy present in a selected band of the total electromagnetic energy that falls on each sensor to thereby produce spectrometric data that may be used by processing circuitry on IC die 102, or be provided to processing circuitry located in another package.

IC die 102 may be attached to a die attach pad (DAP) 104 of a leadframe that includes a set of contacts 105. DAP 104 may also be referred to as a "thermal pad." IC die 100 may also be referred to as a "chip." IC die 102 may be fabricated using known or later developed semiconductor processing techniques. IC die 102 may include an epitaxial (epi) layer on the top surface in which are formed various semiconductor transistor devices and interconnects. One or more conductive layers may be formed on the epi layer and patterned into interconnect traces and bond pads. A set of bond wires 106 may be attached to contacts 105 and bond pads located on the surface of IC die 106 using known or later developed wire bonding techniques. In this example, IC package 100 is a quad-flat no-leads (QFN) package; however, in other embodiments various known or later developed packaging configurations, such as DFN, MLF, SON, flip chips, dual inline packages (DIP), etc, may be fabricated using the techniques disclosed herein to form an encapsulated package with a photonic bandgap structure included within the encapsulant material.

In this example, a solid encapsulant material 120 surrounds and encapsulates IC die 102. A portion of the encapsulation material may include a matrix of interstitial nodes such as indicated at 121 that may be filled with a material that is different from encapsulation material 120. In this example, nodes 121 are arranged in a three dimensional array of spherical spaces that are in turn separated by a lattice of encapsulation material 123. Encapsulation material 123 may be the same or different as solid encapsulation material 120.

In some embodiments, the structure formed by the matrix of nodes 121 and lattice 123 may be referred to herein as a "photonic bandgap structure." A photonic bandgap (PBG) structure formed by periodic nodes 121 may effectively filter photonic energy that falls on package 100 by selectively blocking a frequency band from passing while allowing other electromagnetic photons to pass. In other embodiments, the structure formed by the matrix of nodes 121 and lattice 123 may be referred to herein as a "photonic wave collimator structure." A photonic wave collimator (PWC) structure formed by periodic nodes 121 may effectively filter photonic energy that falls on package 100 by selectively allowing only a certain frequency band of energy to pass.

The PBG works by destructively diffracting energy at a certain band of frequencies. The PWC works by constructively diffracting energy at a certain band of frequencies. It is actually the same phenomenon, just turned on its head. A PWC structure may pass a single band due to the fact that the photonic crystal is designed to work at a narrow band. Just as the PBG can only block a narrow band, the PWC can only pass a narrow band.

In this example, PWC structure 150 may be designed to form a separate photonic wave collimator to each of the three sensors 111-113. Each photonic wave collimator 151, 152, 153 may be designed to allow only a single band of electromagnetic energy received from broad band electromagnetic signal 140 to pass to a corresponding sensor 111-113. In this example, a spectrometer may be provided that may sense energy in three different energy bands of signal 140.

A different spectrometer may be provided by using the same IC die 102, and forming PWC regions with different parameters during the encapsulation process. In this manner, several different devices may be fabricated to sense different bands by using a same version of IC die. Only the encapsulation process needs to be modified to change the spectral sensing parameters by selecting the node and lattice parameters of the photonic wave collimating regions.

While three sensors are illustrated here for clarity, another embodiment may have a larger array of sensors to provide a spectrometer with more precision.

In this example, a broadband electromagnetic signal 140 is impinging on encapsulated package 100. In this example, signal 140 may be an optical signal or a radio frequency signal (RF), for example. For illustrative purposes only, signal 140 is illustrated as having a spectrum of six frequency bands to better illustrate how signal 140 may be separated into different bands by photonic filter structure 150. In reality, the frequencies of a broadband signal are mixed together. Signal 140 may have a broader spectrum or a narrower spectrum than what is included in PWC structure 150, for example.

Solid encapsulant material 120 is typically an epoxy based material that provides mechanical protection and seals IC die 102 from environmental gases and liquids.

In this example, lattice 123 may be in contact at various places across the entire upper surface of IC die 102. As mentioned above, lattice 123 may be formed from the same material as solid encapsulation material 120, or it may be formed using a different material by using an additive manufacturing process. The array of nodes 121 may be formed with one or more different materials. For example, some of the nodes, such as nodes 121, may be filled with a first material and some of the nodes 121 may be filled with different types of material. There may be a number (N) of different materials that are used to fill N different sets of nodes within encapsulation material 123. Node material may be a polymer or other material that has different intrinsic material properties from the lattice material 123. For example, the node material may have various different intrinsic material properties from the lattice material, such as permittivity, permeability, conductivity, etc.

For example, certain nodes 121 may be filled with a high dielectric material, while other nodes 121 are filled with a low dielectric material. In some embodiments, node material 121 may be air, some other gas, or even a vacuum.

In the example of FIG. 1, lattice 123 forms a square three dimensional (3D) array of spherical nodes. In other embodiments, a differently shaped lattice may be formed to produce other shapes of arrays and nodes 121, such as: triangular, rectilinear, hexagonal, round nodes, elongated nodes, tubes, etc.

In some embodiments, die attachment 125 may be a thin layer of adhesive material. In other embodiments, die attachment 125 may include a portion that is also a photonic bandgap structure.

A photonic crystal is an artificially manufactured structure, or material, with periodic constitutive or geometric properties that are designed to influence the characteristics of electromagnetic wave propagation. When engineering these crystals, it is possible to isolate these waves within a certain frequency range. Conversely it may be more helpful to consider these waves as particles and rely on the wave-particle duality throughout the explanation. For this reason, reference to "propagation" herein may refer to either the wave or the particle movement through the substrate. Propagation within this selected frequency range, referred to as the band gap, is attenuated by a mechanism of interferences within the periodic system. Such behavior is similar to that of a more widely known nanostructure that is used in semiconductor applications, a photonic crystal. The general properties and characteristics of photonic structures are known, for example, see: "Fundamental Properties of Phononic Crystal," Yan Pennec and Bahram Djarari-Rouhani, Chapter 2 of "Phononic Crystals, Fundamentals and Applications" 2015, which is incorporated by reference herein. See also "Self-Collimating Phenomena in Photonic Crystals," Hideo Kosaka et al, 1999.

Photonic crystals may be formed by a periodic repetition of inclusions in a matrix. The dielectric properties, shape, and arrangement of the scatterers may strongly modify the propagation of the electromagnetic waves in the structure. The photonic band structure and dispersion curves can then be tailored with appropriate choices of materials, crystal lattices, and topology of inclusions.

Similarly to any periodic structure, the propagation of electromagnetic waves in a photonic crystal is governed by the Bloch or Floquet theorem from which one can derive the band structure in the corresponding Brillouin zone. The periodicity of the structures, that defines the Brillouin zone, may be in one (1D), two (2D), or three dimensions (3D).

The general mechanism for the opening of a band gap is based on the destructive interference of the scattered waves by the inclusions. This necessitates a high contrast between the properties of the materials. In periodic structures, this is called the Bragg mechanism and the first band gap generally occurs at a frequency which is about a fraction of c/a, where "c" is a typical velocity of light, and "a" is the period of the structure.

Photonic bandgap structures may be designed and modeled using simulation software available from various vendors. For example, physics-based systems may be modeled and simulated using COMSOL Multiphysics® simulation software from COMSOL®. "Multiphysics" and "COMSOL" are registered trademarks of COMSOL AB. HFSS (High Frequency Structure Simulator) is available from Ansys. CST (Computer Simulation Technology) offers several simulation packages.

Figure 2A:
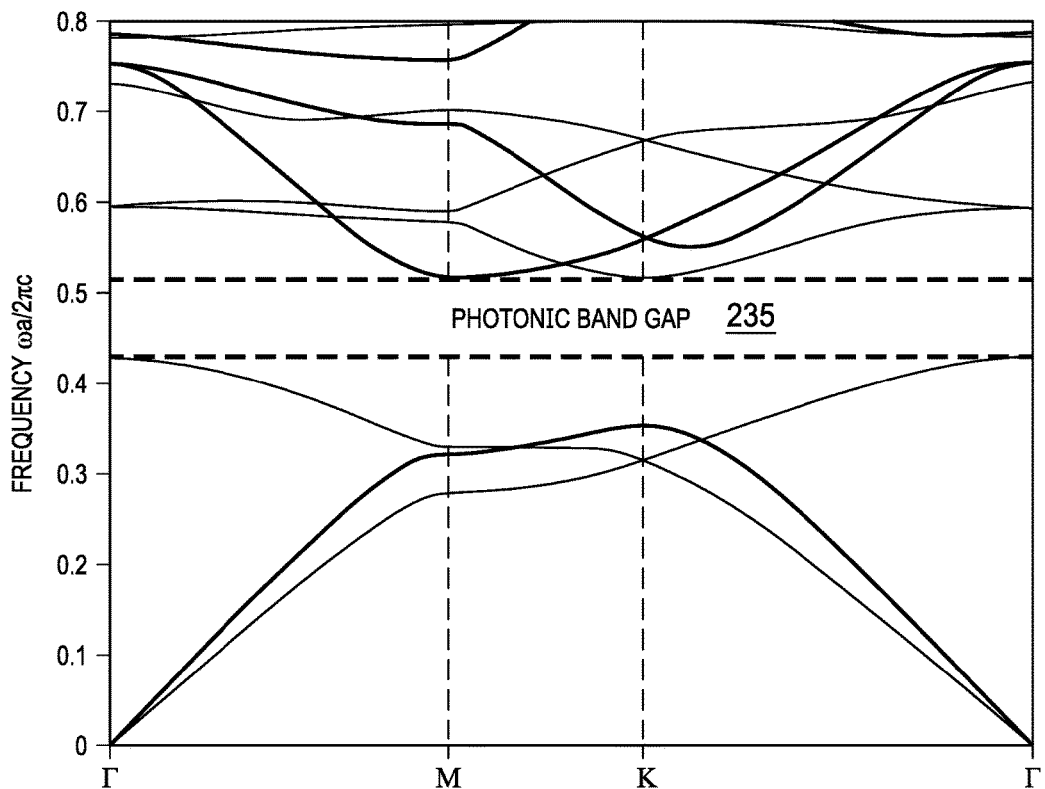
FIGS. 2A-2C is a frequency dispersion plot illustrating a band gap in a photonic bandgap structure having a hexagonal lattice.
Figure 2B:
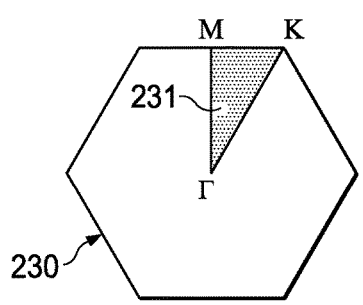
Figure 2C:
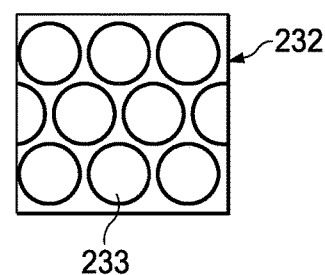
Figure 3:
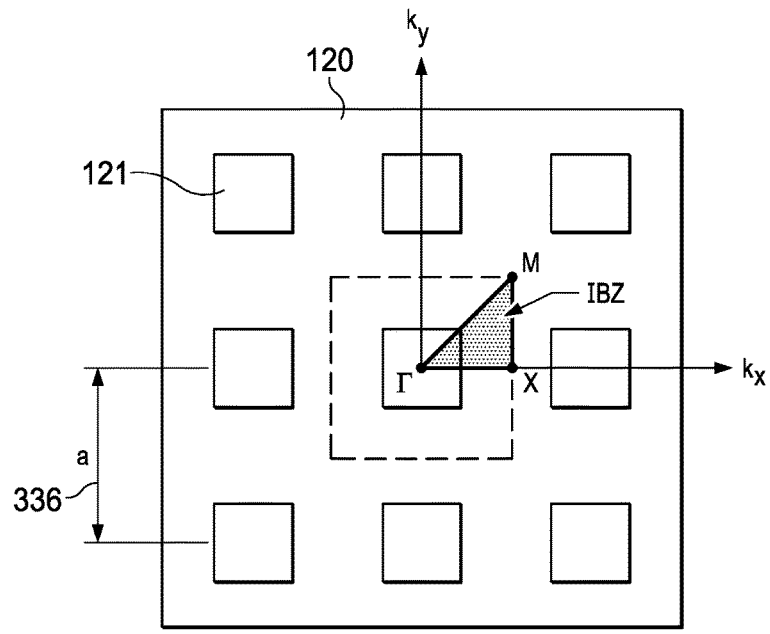
FIG. 3 is an example of another photonic bandgap structure having a square lattice.

FIG. 2A is a frequency dispersion plot illustrating a band gap in a photonic bandgap structure having a hexagonal lattice. FIG. 2B illustrates a single cell 230 of the hexagonal matrix and illustrates Brillouin zone 231 for the hexagonal cell. FIG. 2C illustrates a larger portion of a hexagonal photonic crystal 232 formed by a 3D matrix of nodes as indicated at 233. FIG. 3 is an example of another photonic bandgap structure having a square lattice.

The x-axis of FIG. 2A represents the periphery of Brillouin zone 231 of photonic crystal 232 as defined by points r, M, and K. The y-axis represents the angular frequency of acoustic energy propagating in photonic crystal 232 in units of $\omega a/2\pi C$. The various plot lines represent propagation paths through Brillouin zone 231. Region 235 represents a photonic band gap in which the propagation of waves falling within the defined band of frequencies is blocked by interference produced by the crystal lattice.

The width and the frequency range covered by a photonic bandgap depends on the periodic spacing of the nodes 233, which may be represented by lattice constant "a" as indicated at 336 in FIG. 3, and the relative difference between the dielectric constant of the lattice material and the dielectric constant of the nodes. For example, the frequency range covered by photonic bandgap 235 may be shifted to a higher frequency range for larger relative differences between the dielectric constant of the lattice and the dielectric constant of the nodes, while the photonic bandgap 235 may be shifted to a lower frequency range for smaller relative differences between the dielectric constant of the lattice and the dielectric constant of the nodes.

Figure 4:
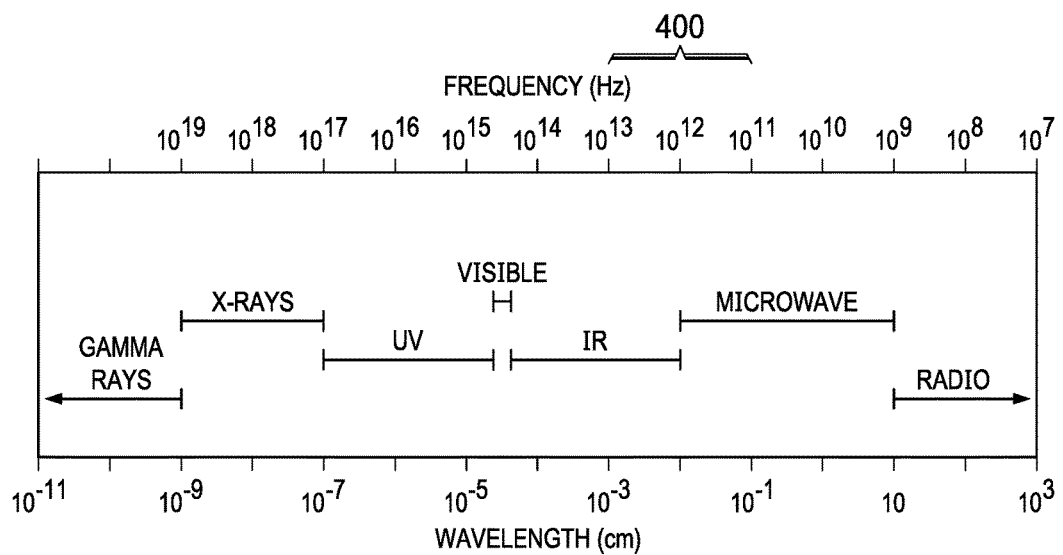
FIG. 4 is a plot illustrating a portion of the electromagnetic frequency spectrum vs. wavelength.

FIG. 4 is a plot illustrating a portion of the electromagnetic frequency spectrum vs. wavelength for an example dielectric solid material. The velocity (v) of an electromagnetic wave in a vacuum is approximately equal to the speed of light (c) in a vacuum, which is approximately $3 \times 10^8$ m/s. The velocity of an electromagnetic wave through a solid material is defined by expression (1), where $\varepsilon_r$ is the relative permittivity of the solid material, which may also be referred to as the "dielectric constant" of the material $$v = c/\sqrt{\varepsilon r} \quad (1)$$

The photonic wavelength ($\lambda$) may be determined using expression (2), where the velocity (v) in dielectric materials is typically on the order of $1\text{-}2.5 \times 10^8$ m/s for dielectric constant values in the range of approximately 1-10, and f is the frequency of the photon.

$$\text{lambda } (\lambda) = v/f \quad (2)$$

For electromagnetic signals in the GHz to low THz frequency range, for example, the corresponding wavelengths in encapsulant material 120 may be in the range of several microns to several hundred microns, as indicated at 400. The opening of wide photonic band gaps requires two main conditions. The first one is to have a large physical contrast, such as density and speed of propagation of the wave movements, between the nodes and the lattice. The second condition is to present a sufficient filling factor of the nodes in the lattice unit cell. The forbidden band gap occurs in a frequency domain given by the ratio of an effective propagation velocity in the composite material to the value of the lattice parameter of the periodic array of nodes. Referring to FIG. 3, as a rule of thumb the lattice dimension 336 may be selected to be about one half of the wavelength of the center of the target photonic bandgap.

While the effect of dielectric constant ($\varepsilon r$) is described above, other intrinsic properties of a material may be evaluated during the design of a PBG structure, such as permeability, conductivity, etc.

Figure 5:
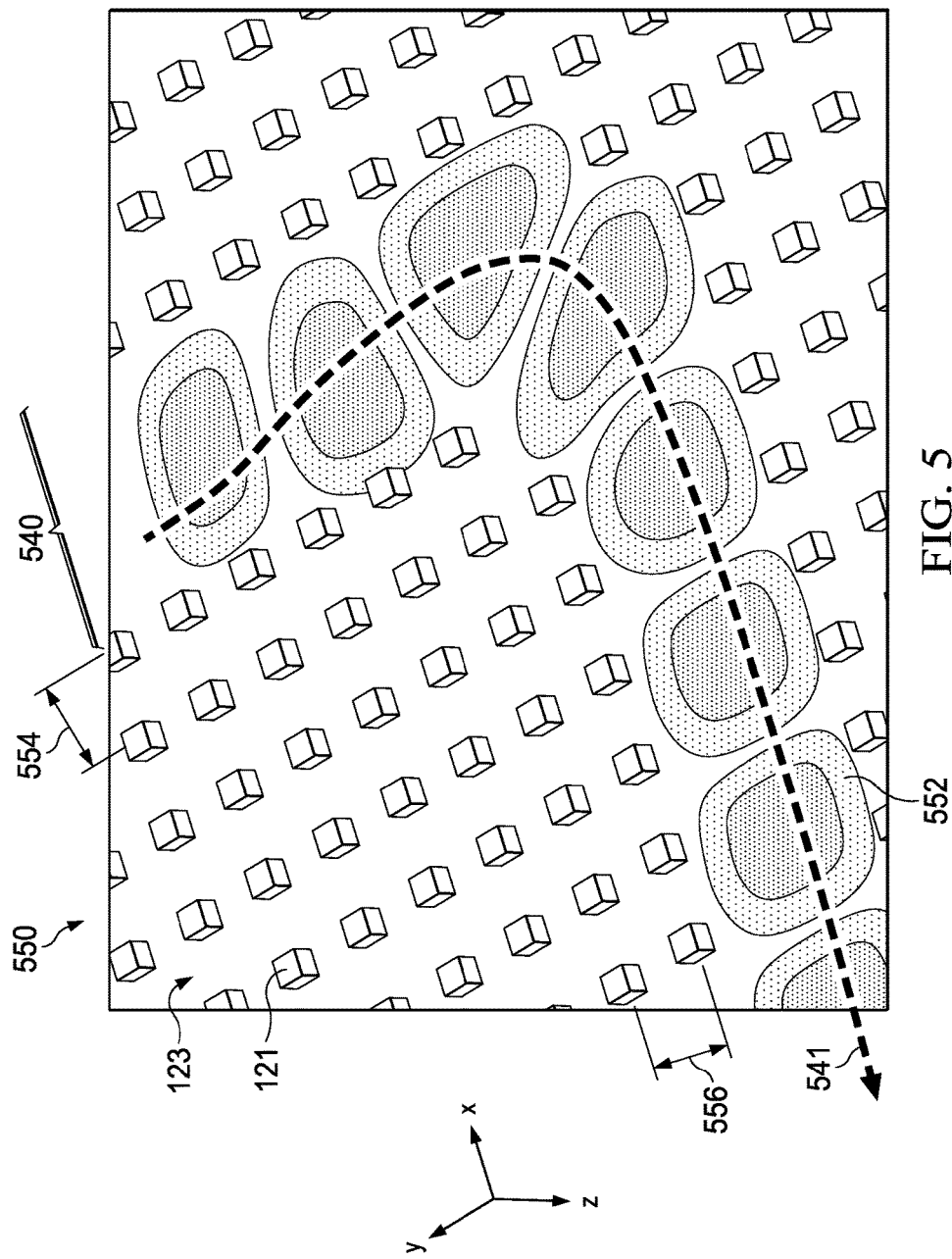
FIG. 5 illustrates a simulation of an example photonic waveguide formed by a photonic bandgap structure.

FIG. 5 illustrates a simulation of an example PBG waveguide 540 formed by an example photonic bandgap structure 550. This example illustrates a how photons of a particular frequency may move through a waveguide region 540 of a PBG structure 550 while being blocked from another region. As described above, a photonic bandgap structure may be formed within encapsulation material 123 by inserting a matrix of nodes 121 with a periodic spacing. In this example, the x-axis node spacing 554 is approximately equal to the y-axis node spacing 556. The z-axis node spacing (not shown) is also approximately the same as node spacing 554, 556 in this example.

The node spacing 554-556 in this example may be selected to be approximately one half the wavelength of a selected frequency of electromagnetic radiation represented by photons 552 that should be guided by bandgap structure 550. In this manner, electromagnetic energy in the form of photons 552 that falls within the bandgap frequency range of PBG structure 550 may be guided through PBG waveguide 540 is illustrated by signal vector 541.

Figure 6:
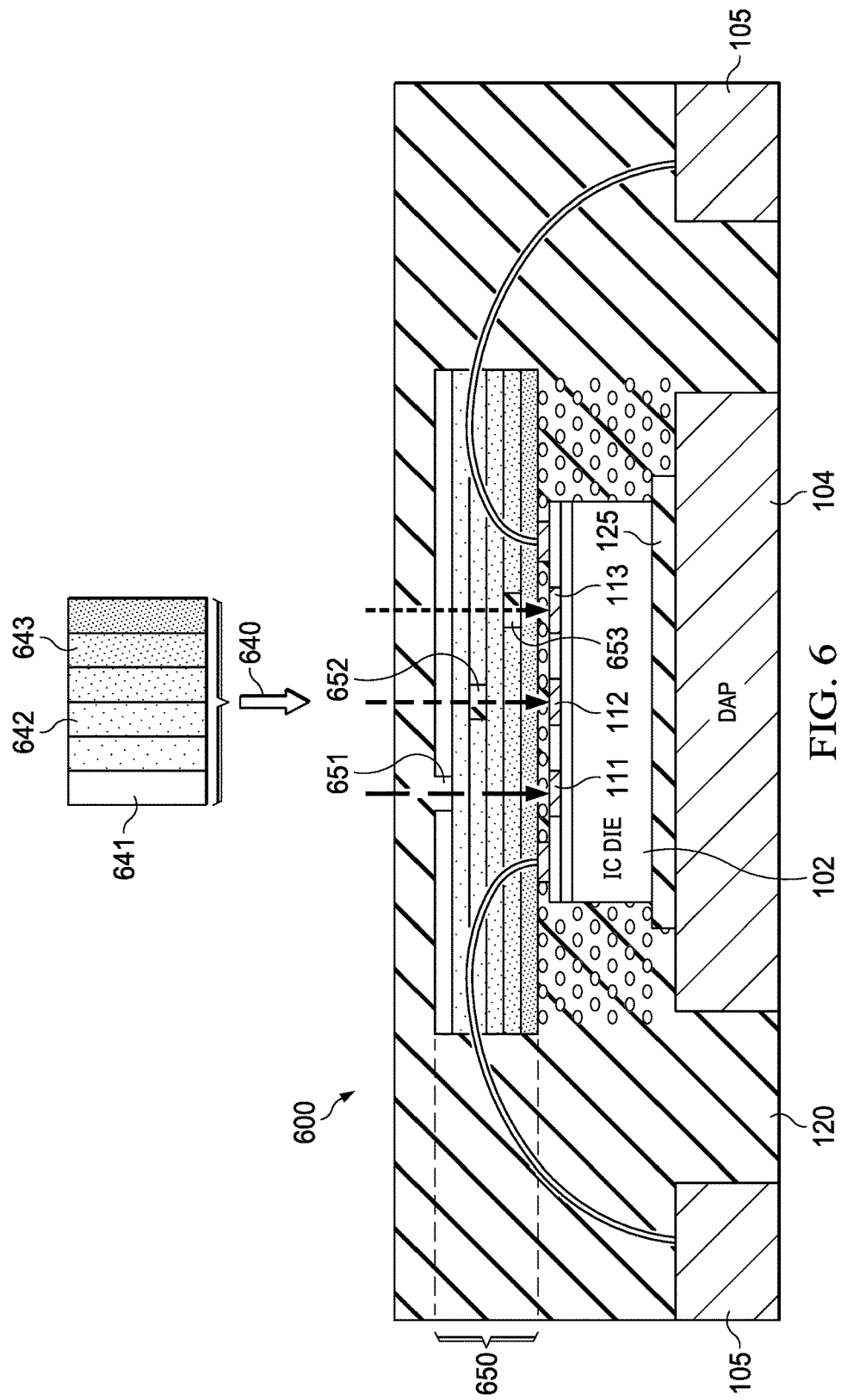
FIG. 6 is a cross section of an example encapsulated package that includes another example of a photonic filter structure.

FIG. 6 is a cross sectional view of encapsulated package 600 that includes an embodiment of a spectrometer that uses filter structure 650 that is formed within the encapsulation material 120 by a multilayer PBG structure. In this example, filter structure 650 may be implemented in only a limited portion of encapsulation material 120, but still provide an effective filter for electromagnetic energy that falls on package 600. In this example, filter structure 650 includes six layers that are designed to provide a photonic bandgap at six different frequency bands, however, in other embodiments a larger or a smaller number of layers may be implemented to provide a smaller or larger number of bandgaps.

In this example, a broadband electromagnetic signal 640 is impinging on encapsulated package 600. In this example, signal 640 may be an optical signal or a radio frequency signal (RF), for example. For illustrative purposes only, signal 640 is illustrated as having a spectrum of six frequency bands, such as band 641, 642, 643, to correspond to the six bandgaps provided by the six layer filter structure 650. Signal 640 may have a broader spectrum or a narrower spectrum than what is included in multilayer filter structure 650, for example.

Assuming the bandgap of each of the six layers of filter structure 650 is designed cover a different portion of the spectrum and all six together can block the entire spectrum, then no portion of signal 640 would reach any of sensors 111-113. However, in this example, a waveguide region may be formed in selected layers of filter structure 650 to allow energy in a selected band to flow through filter structure 650. For example, a waveguide region 651 may be formed in one layer of filter structure 650 to allow frequencies in a selected band, such as the band indicated at 641, to flow through the filter structure and be sensed by sensor 111. Another waveguide region 652 may be formed in another layer of filter structure 650 to allow frequencies in another selected band, such as the band indicated at 642, to flow through the filter structure and be sensed by sensor 112. Similarly, waveguide region 653 may be formed in another layer of filter structure 650 to allow frequencies in another selected band, such as the band indicated at 643, to flow through the filter structure and be sensed by sensor 113. In this example, a spectrometer may be provided that may sense energy in three different energy bands in signal 640.

A different spectrometer may be provided by using the same IC die 102, and forming waveguide regions in different layers of filter structure 650 during the encapsulation process. In this manner, several different devices may be fabricated to sense different bands by using a same type of IC die. Only the encapsulation process needs to be modified to change the spectral sensing parameters by selecting which layers to place wave guide regions. In some embodiments, waveguide regions may be placed in several layers to allow a sensor to sense energy for more than one band.

While three sensors are illustrated here for clarity, another embodiment may have a larger array of sensors to provide a spectrometer with more precision.

While a filter structure 650 is illustrated herein that has approximately contiguous bandgaps, another embodiment may use a filter structure in which the bandgaps are not contiguous. In that case, electromagnetic energy that is not blocked by any bandgap in the bandgap structure may be sensed by an underlying sensor. In some embodiments, a separate portion of the filter over each sensor may be tailored to have no bandgap in the frequency range intended to be sensed by each sensor.

Figure 7:
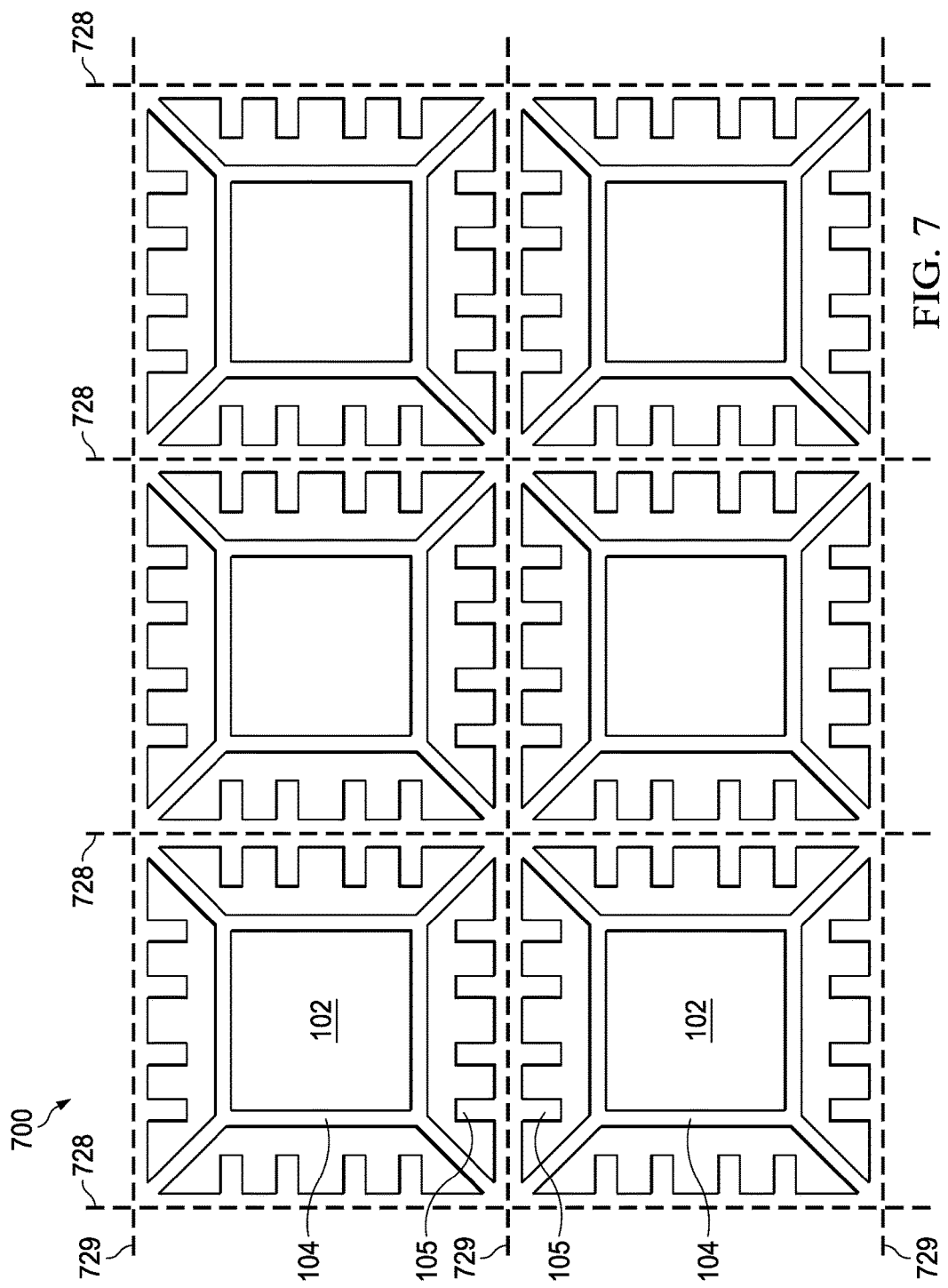
FIG. 7 is a top view of an example leadframe.

FIG. 7 is a top view of an example QFN leadframe 700 that may be used to support IC 100 in FIG. 1, for example. Other types of packages may use a leadframe strip that has a different known or later developed configuration. Lead frame strip 700 may include one or more arrays of individual lead frames. Lead frame strip 700 is typically fabricated from a copper sheet that is etched or stamped to form a pattern of thermal pads and contacts. Lead frame strip 700 may be plated with tin or another metal that will prevent oxidation of the copper and provide a lower contact surface that is easy to solder. An IC die may be attached to each individual lead frame.

Each individual leadframe may include a die attach pad, such as die attach pads 104. Each individual lead frame also includes a set of contacts that surround the die attach pad, such as contacts 105. A sacrificial strip of metal connects all of the contacts together and provides mechanical support until a sawing process removes it. An IC die, also referred to as a "chip," is attached to each die attach pad during a packaging process. Wire bonding may then be performed to connect bond pads on each IC chip to respective contacts on the lead frame. The entire lead frame strip 700 may then be covered with a layer of mold compound using an additive process as described in more detail below to encapsulate the ICs. Lead frame strip 700 may then be singulated into individual packaged ICs by cutting along cut lines 728, 729.

Figure 8A:
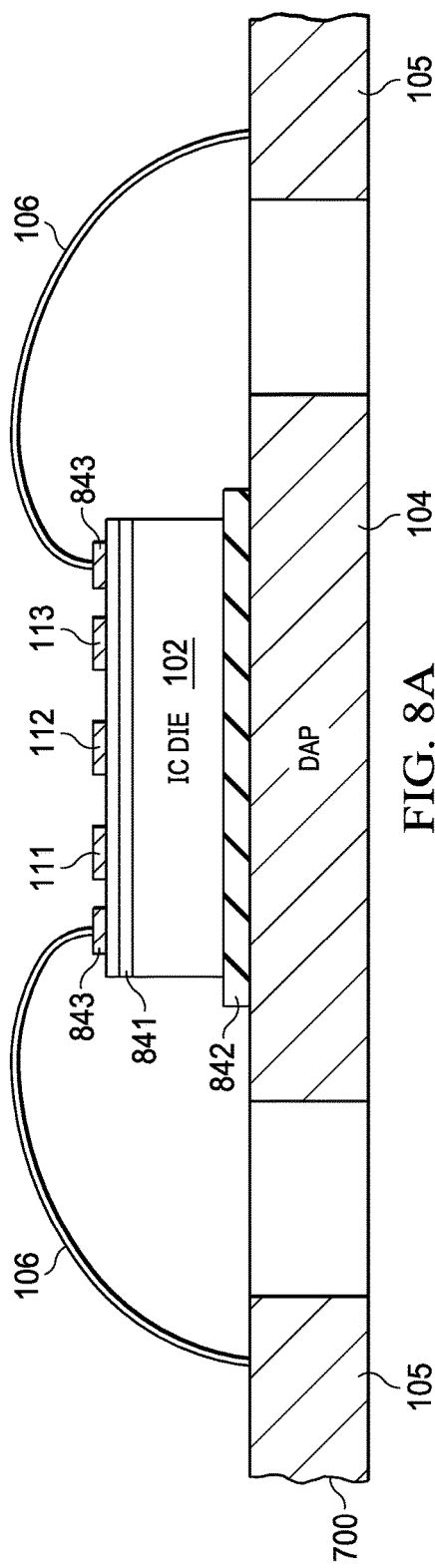
FIGS. 8A-8C illustrate formation of a photonic filter structure using an additive manufacture process to encapsulate an IC.
Figure 8B:
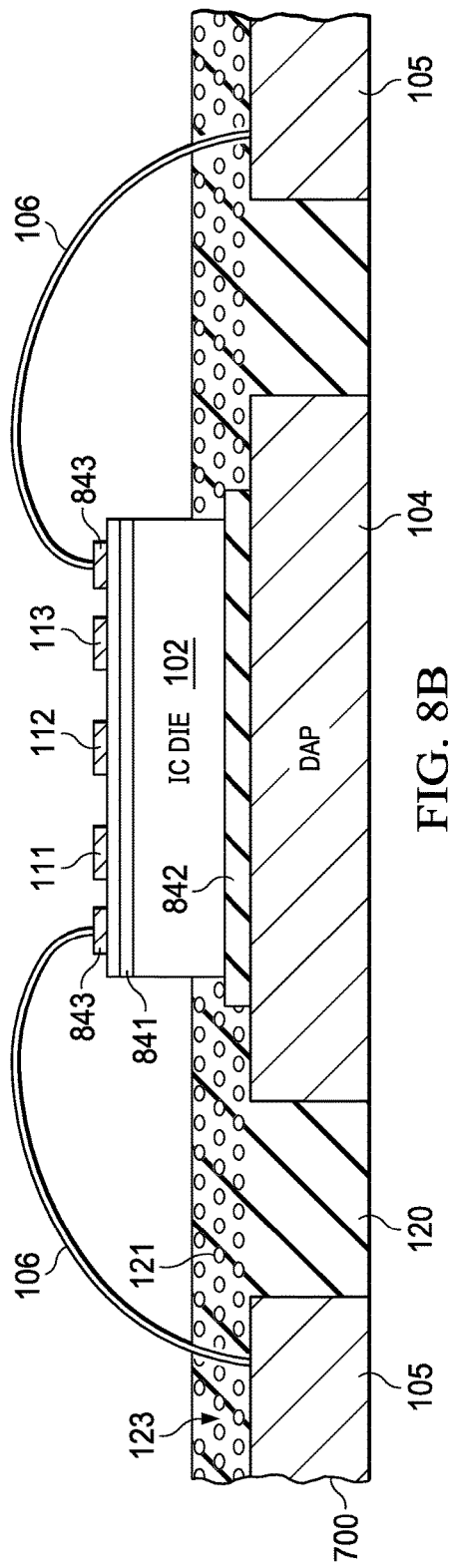
Figure 8C:
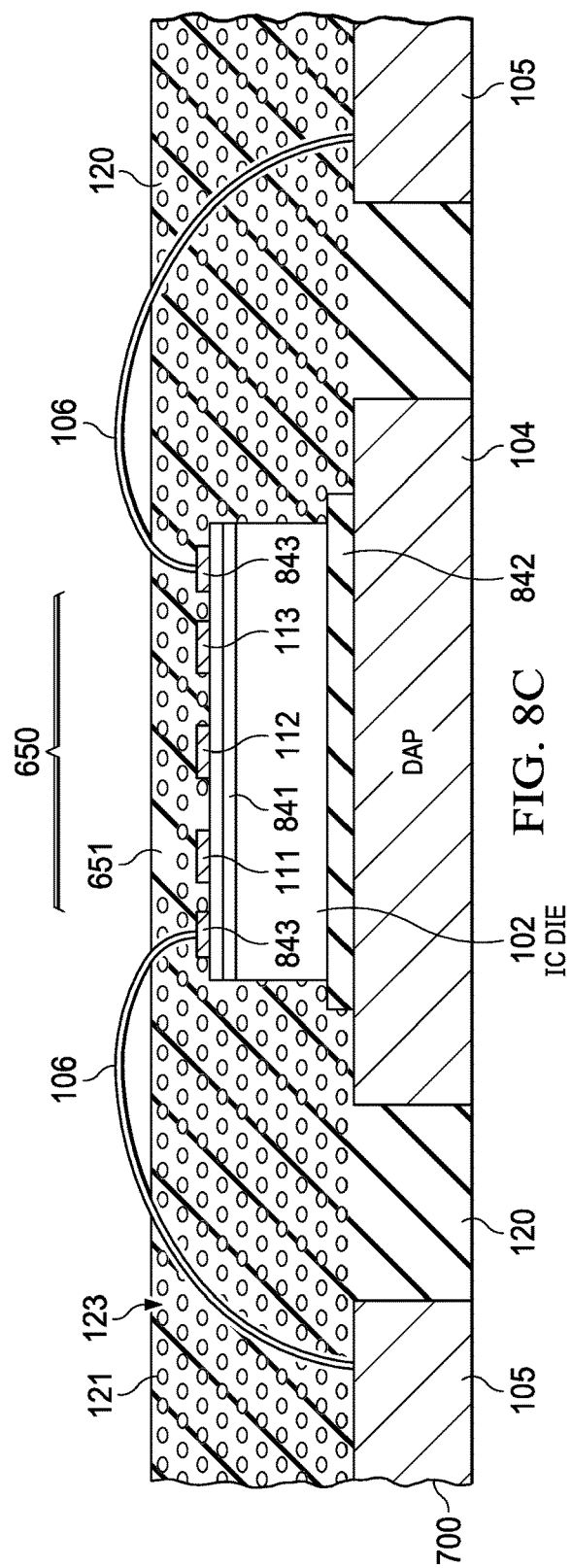

FIGS. 8A-8C are cross sectional views illustrating fabrication of the example IC package 100 of FIG. 1. IC die 102 may be attached by die attach layer 842 to a die attach pad 104 of a leadframe that may be part of a leadframe strip similar to leadframe strip 700 shown in FIG. 7 that includes a set of contacts 105. IC die 102 may be fabricated using known or later developed semiconductor processing techniques. IC die 102 may include an epitaxial (epi) layer 841 on the top surface in which are formed various semiconductor transistor devices and interconnects. One or more conductive layers may be formed on the epi layer and patterned into interconnect traces and bond pads 843. A set of bond wires 106 may be attached to contacts 105 and bond pads 843 located on the surface of IC die 102 using known or later developed electrical connection techniques. In this example, IC package 100 is a quad-flat no-leads (QFN) package; however, in other embodiments various known or later developed packaging configurations, such as DFN, MLF, SON, flip chip, dual inline packages (DIP), etc, may be fabricated using the techniques disclosed herein to form an encapsulated package with a PBG waveguide formed within the encapsulant material.

FIG. 8B is a cross sectional view illustrating partial formation of encapsulation material 120. Additive manufacturing processes are now being used in a number of areas. The International Association for Testing Materials (ASTM) has now promulgated ASTM F7292-12a "Standard Terminology for Additive Manufacturing Technologies" 2012 which is incorporated by reference herein. Currently, there are seven families of additive manufacturing processes according to the ASTM F2792 standard, including: vat photopolymerization, powder bed fusion, binder jetting, material jetting, sheet lamination, material extrusion, directed energy deposition. Hybrid processes may combine one or more of these seven basic processes with other manufacturing processes for additional processing flexibility. Recent process advances allow additive manufacturing of 3D structures that have feature resolution of less than 100 nm, such as direct laser lithography, multi-photon lithograph, two-photon polymerization, etc.

In this example, a vat photopolymerization process may be used in which leadframe strip and the ICs attached to it, such as IC die 102, are lowered into a vat of liquid photopolymer resin. A light source, such as a laser or projector, may then expose selected regions of the liquid photopolymer resin to initiate polymerization that converts exposed areas of the liquid resin to a solid. In this manner, layers of encapsulant material 120 may be formed in selected shapes. For example, encapsulant material that forms lattice 123 may be the same or different as the solid encapsulant material 120. Nodes 121 may be formed with any selected lattice spacing.

FIG. 8C is a cross sectional view illustrating further partial formation of encapsulation material 120 around IC die 102. Additional layers of liquid encapsulation material 120 have been exposed and converted to a solid. Selective exposure of the liquid resin allows lattice 123 to be formed with nodes 121, as described with regard to FIG. 1. A small portion of filter structure 150 is illustrated in FIG. 8C. Waveguide region 651 may be formed in this example by omitting nodes 123 from the encapsulation material in the region that forms waveguide 651.

As each layer of encapsulation material is added, the lattice and/or node parameters may be altered to form a multilayer filter structure in which each layer provides a different bandgap.

The leadframe strip may be submerged in different vats at different times in order to allow different materials to form the nodes 121 within lattice 123.

Additional layers of resin may be exposed and hardened to form the final outside encapsulation layer illustrated in FIG. 1. The leadframe strip may then be sawed or otherwise separated into individual encapsulated IC packages.

In another embodiment, other additive manufacturing processes may be used to form encapsulation material 120. For example, a powdered bed diffusion process may be used in which a powdered material is selectively consolidated by melting it together using a heat source such as a laser or electron beam.

In another embodiment, a material jetting process may be used in which droplets of material are deposited layer by layer to produce a PBG waveguide within an encapsulation structure as described herein. However, bond wires 106 may require extra care to avoid disrupting the droplet streams.

In another embodiment, bond wires are not initially bonded to contacts 105 and bond pads 843. In this example, a material jetting process may be used in which droplets of material are deposited layer by layer to produce a photonic bandgap structure as described herein. As part of the material jetting process, a conductive material may be deposited to form the bond wires between contacts 105 and bond pads 843. In some embodiments, a sintering process may be done by heating the encapsulated leadframe 700 assembly to further solidify the bond wires. The leadframe strip 700 may then be sawed or otherwise separated into individual encapsulated IC packages.

In another embodiment, IC die 102 is not initially attached to die attach pad 104 of a leadframe that may be part of a leadframe strip similar to leadframe strip 700 shown in FIG. 7. In this example, a vat photopolymerization process may be used in which the leadframe strip is lowered into a vat of liquid photopolymer resin. A light source, such as a laser or projector, may then expose selected regions of the liquid photopolymer resin to initiate polymerization that converts exposed areas of the liquid resin to a solid. In this manner, layers of encapsulant material 120 may be formed in selected shapes. In this manner, a photonic bandgap structure 126 as shown in FIG. 1 may be fabricated on top of die attach pad 104 to isolate a later attached IC die from die attach pad 104. Spaces may be left above each contact 105 for later attachment of bond wires. A set of bond wires 106 may be attached to contacts 105 and bond pads 643 located on the surface of IC die 106 using known or later developed wire bonding techniques. Additional layers of resin may be exposed and hardened to form an additional photonic structure as described with regard to FIGS. 8A-8C, for example. The leadframe strip may then be sawed or otherwise separated into individual encapsulated IC packages.

In another embodiment, the photonic bandgap structure may be fabricated using a lattice material that includes filler particles diffused throughout the lattice material in place of the explicitly formed nodes as described above, such as nodes 121. In this case, the filler particles are selected to have a size and material composition that will influence the characteristics of electromagnetic wave propagation, as described above. The filler material may be a polymer or other material that has different intrinsic material properties from the lattice material, in a similar manner as the difference between nodes 121 and lattice material 123. In some embodiments, the filler material may have a higher dielectric constant than the lattice material, while in other embodiments the filler material may have a lower dielectric constant than the lattice material, for example.

In another embodiment, multiple photonic bandgaps may be formed by using two or more types of fillers. For example, a portion of the filler material may have a high dielectric constant, while another portion of the filler material may have a low dielectric constant. In some embodiments, different size filler particle may be used in different regions or in a same region to form multiple bandgaps. In some embodiments, a different number of filler particles per unit volume may be used in different regions to form different bandgaps.

In this case, the filler dispersion may not be perfectly crystalline, but there will be a statistical mean separation of the filler particle that may lend itself to a bandgap based on the statistical mean separation distance of the filler particles.

An additive manufacturing process may be used to encapsulate an IC die using two or more different polymers, such as one with filler particles and one without filler particles to form the PBG structures as described herein or other configurations of PBG structures.

Alternatively, a selective molding process may be used in which one area of the encapsulation is molded with first polymer having either no filler particles or a first configuration of filler particles (size, material, number of particles per unit volume, etc.) and other areas are molded with a polymer having a different filler particle configuration to form a PBG structure as described herein or other configurations of PBG structures.

Figure 9A:
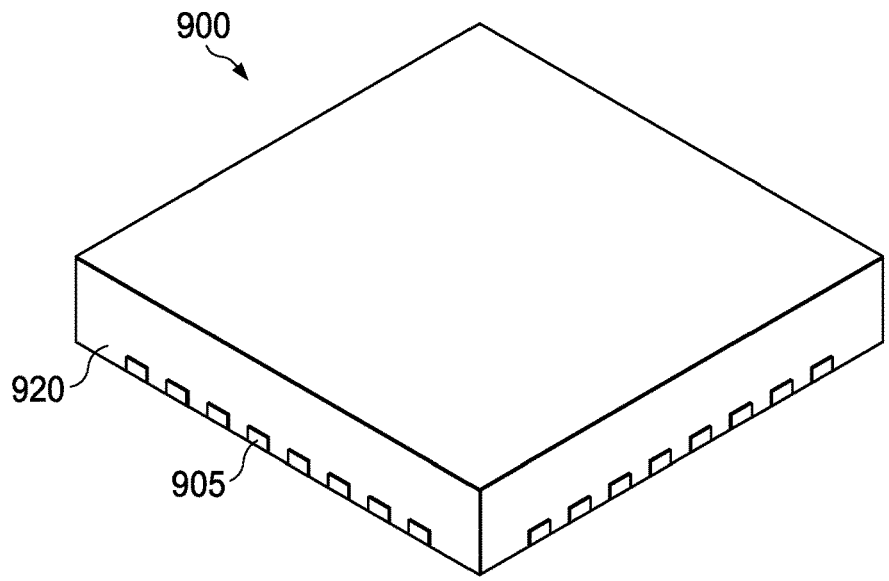
FIGS. 9A-9B illustrate a top and bottom view of an example IC package containing a photonic filter structure.
Figure 9B:
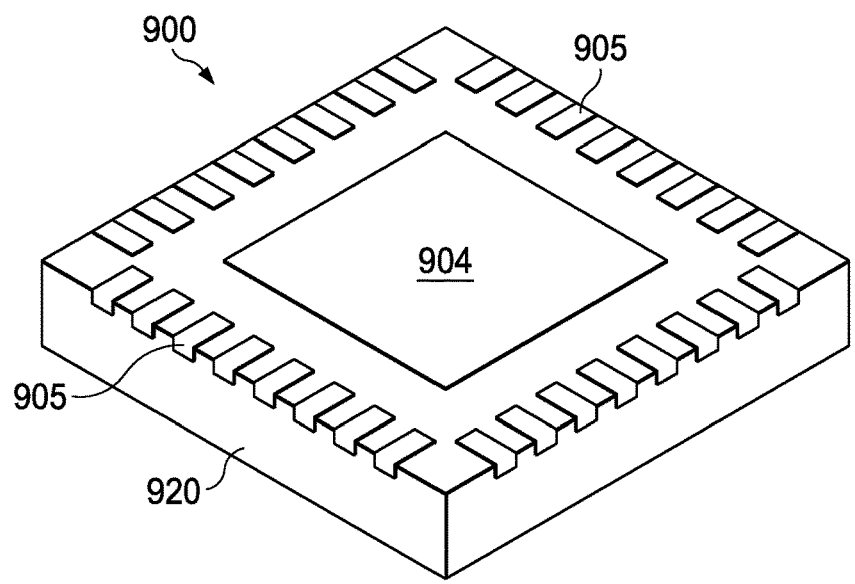

FIGS. 9A-9B are top and bottom views of an example IC package 900 that includes a PBG waveguide provided by a photonic bandgap structure within the encapsulant material as described herein. IC 900 is an illustration of a quad-flat no-leads (QFN) IC package that was encapsulated using additive manufacturing process to form PBG waveguide structures within the encapsulation material as described herein. FIG. 9A illustrates a top side and FIG. 9B illustrates a bottom side of QFN package 900. Flat no-leads packages such as quad-flat no-leads (QFN) and dual-flat no-leads (DFN) physically and electrically connect integrated circuits to printed circuit boards. Flat no-leads, also known as micro leadframe (MLF) and SON (small-outline no leads), is a surface-mount technology, one of several package technologies that connect ICs to the surfaces of PCBs without through-holes. Flat no-lead is a near chip scale plastic encapsulation package made with a planar copper lead frame substrate. Perimeter lands on the package bottom provide electrical connections to the PCB. Flat no-lead packages include an exposed thermal pad 904 to improve heat transfer out of the IC (into the PCB). Heat transfer can be further facilitated by metal vias in the thermal pad. The QFN package is similar to the quad-flat package, and a ball grid array.

QFN package 900 includes a set of contacts 905 arrayed around the perimeter of the package on the bottom side. Thermal pad 904 has an exposed surface on the bottom side of QFN 900. An integrated circuit die (not shown) is mounted to the other side of thermal pad 904. The entire assembly is encapsulated in an encapsulation material 920 using a manufacturing process as described herein to form a photonic filter structure. While a QFN is illustrated in FIGS. 9A-10B, other embodiments may use other types of integrated circuit packages.

Figure 10:
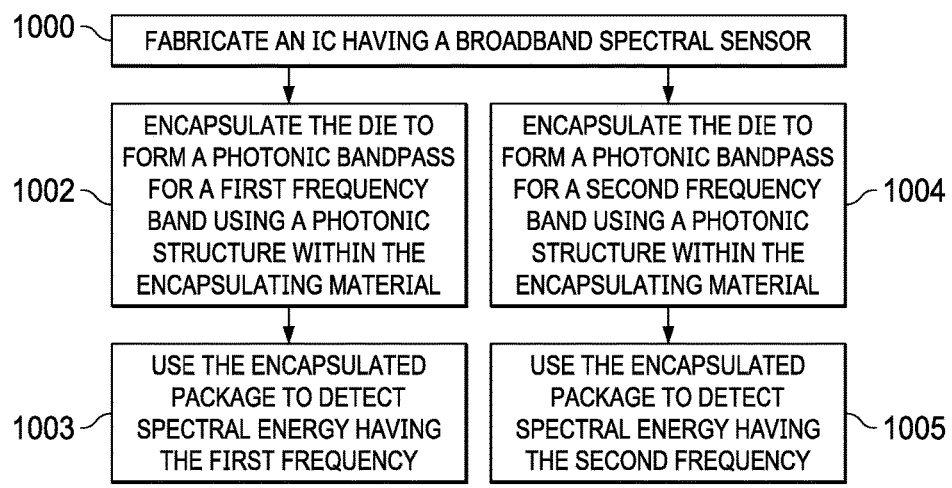
FIG. 10 is a flow chart illustrating an example process for formation of an encapsulated package with a photonic filter structure within the encapsulation material.

FIG. 10 is a flow diagram illustrating fabrication of the example encapsulated package of FIG. 1. In one embodiment, as described above in more detail, an IC die may be fabricated that has one or more broadband spectral sensors, such as sensor 111-113 as illustrated in FIG. 6, as indicated at 1000. The IC die may be fabricated using known or later developed semiconductor processing techniques. The IC die may include an epitaxial (epi) layer on the top surface on which are formed various semiconductor transistor devices and interconnects. One or more conductive layers may be formed on the epi layer and patterned into interconnect traces and bond pads. A set of bond wires may be attached to the contacts and bond pads located on the surface of the IC die using known or later developed wire bonding techniques.

An example of the IC die may be encapsulated to form an encapsulated package that includes a filter structure that passes only a selected frequency band of energy to the one or more sensors on the IC die, as indicated at 1002. The filter structure may be any of the photonic filter structures disclosed herein or later developed structures, such as photonic wave collimating structure, such as filter structure 150 as shown in FIG. 1; a multilayer filter structure, such as filter structure 650 as shown in FIG. 6, etc. A band(s) may be selected by selective placement of waveguides in the multiple layers, as described above in more detail. A waveguide region may be formed during the encapsulation process by simply omitting nodes from the region that forms the waveguide. As described above in more detail, the filter structure is formed within the encapsulation material of the package.

The encapsulated package may then be used to detect spectral energy in the selected band(s) defined by the filter structure, as indicated at 1003.

Another example of the same version of the IC die may be encapsulated to form an encapsulated package that includes a filter structure that passes a different selected frequency band of energy to the one or more sensors on the IC die, as indicated at 1004. The filter structure may be any of the photonic filter structures disclosed herein or later developed structures. A band(s) may be selected by selective placement of waveguides in the multiple layers, as described above in more detail. As described above in more detail, the filter structure is formed within the encapsulation material of the package.

The encapsulated package may then be used to detect spectral energy in the selected band(s) defined by the filter structure, as indicated at 1005.

In this manner, several different versions of spectrometer devices may be manufactured using a common IC die by merely changing the filter structure parameters during the encapsulation process.

In each case, a first portion of the encapsulation material may be solid and a second portion of the encapsulation material may include nodes filled with a second material to form a photonic bandgap structure. As described above in more detail, an additive manufacturing process may be used to create a lattice and fill the periodically spaced nodes in the lattice with a different type of material, or with several different types of material in different locations. A waveguide may be formed during the encapsulation process by simply omitting nodes from the region that forms the waveguide.

In another embodiment, the encapsulation process indicated at box 1002, 1004 may be done using a selective molding process in which one area of the encapsulation is molded with first polymer having either no filler particles or a first configuration of filler particles (size, material, number of particles per unit volume, etc.) and other areas are molded with a polymer having a different filler particle configuration diffused within the polymer to form a photonic filter structure as described herein or other configurations of photonic filter structures.

As discussed above in more detail, various types of IC packages may be formed in this manner. For example, a quad-flat no-leads (QFN) package is illustrated in FIG. 1. However, in other embodiments various known or later developed packaging configurations, such as DFN, MLF, SON, flip-chips, dual inline packages (DIP), etc, may be fabricated using the techniques disclosed herein to form an encapsulated package with a PBG waveguide included with the encapsulant material.

Figure 11:
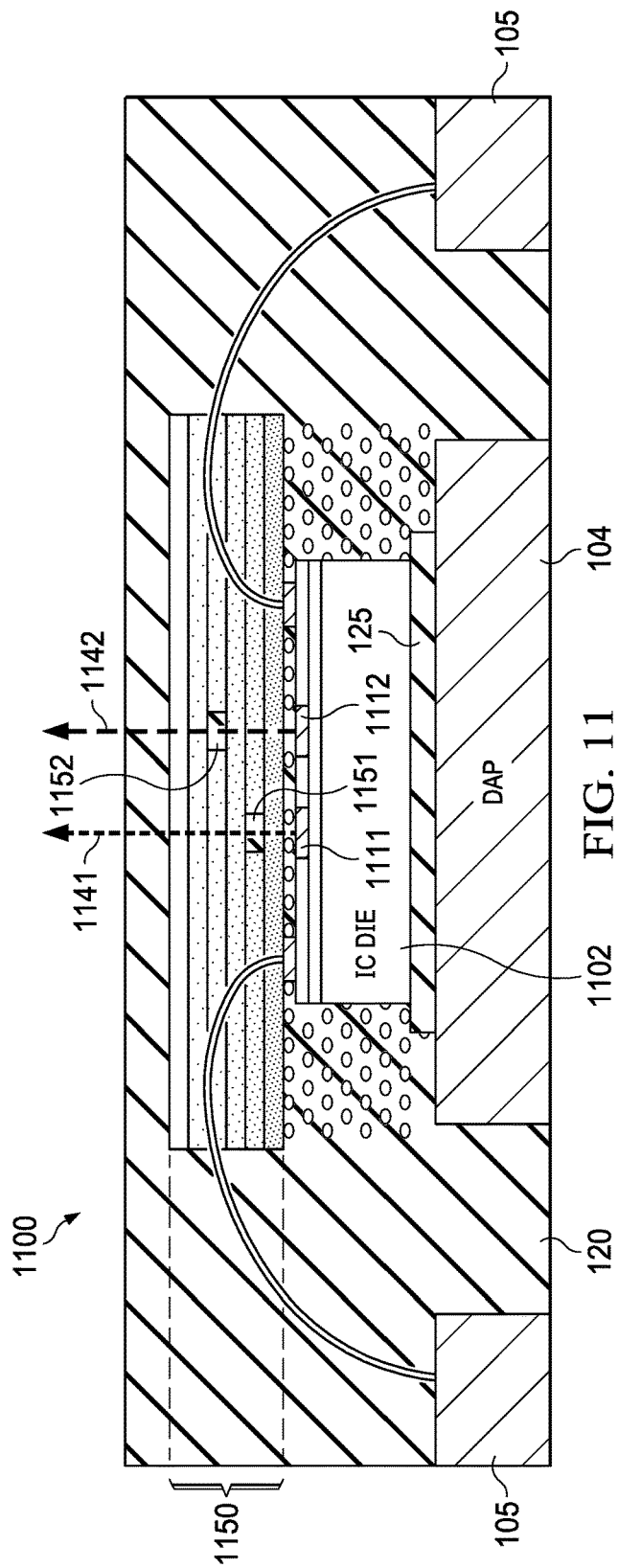
FIGS. 11-12 are a cross sectional views of an alternative embodiments.

FIG. 11 is a cross sectional view of an example encapsulated package 1100 that includes a multilayer filter structure 1150. In this example, IC die 1102 includes two broadband emitter circuits 1111, 1112. Emitter devices 1111, 1112 may be optical or RF emitters, for example. While two emitters are illustrated in this example, another embodiment may have only a single emitter, or three or more emitters.

Filter structure 1150 may be fabricated during encapsulation of IC die in a similar manner as described above with regard to FIGS. 8A-8C. By selectively placing waveguide regions 1151, 1152 in a selected bandgap layer(s) of multilayer filter structure 1150, a particular band may be selected to be emitted by each emitter device 1111, 1112 of package 1100, as indicated at 1141, 1142.

In another embodiment, another type of photonic filter structure may be used in place of filter structure 1150, such as a photonic wave collimating structure similar to PWC structure 150, for example.

Figure 12:
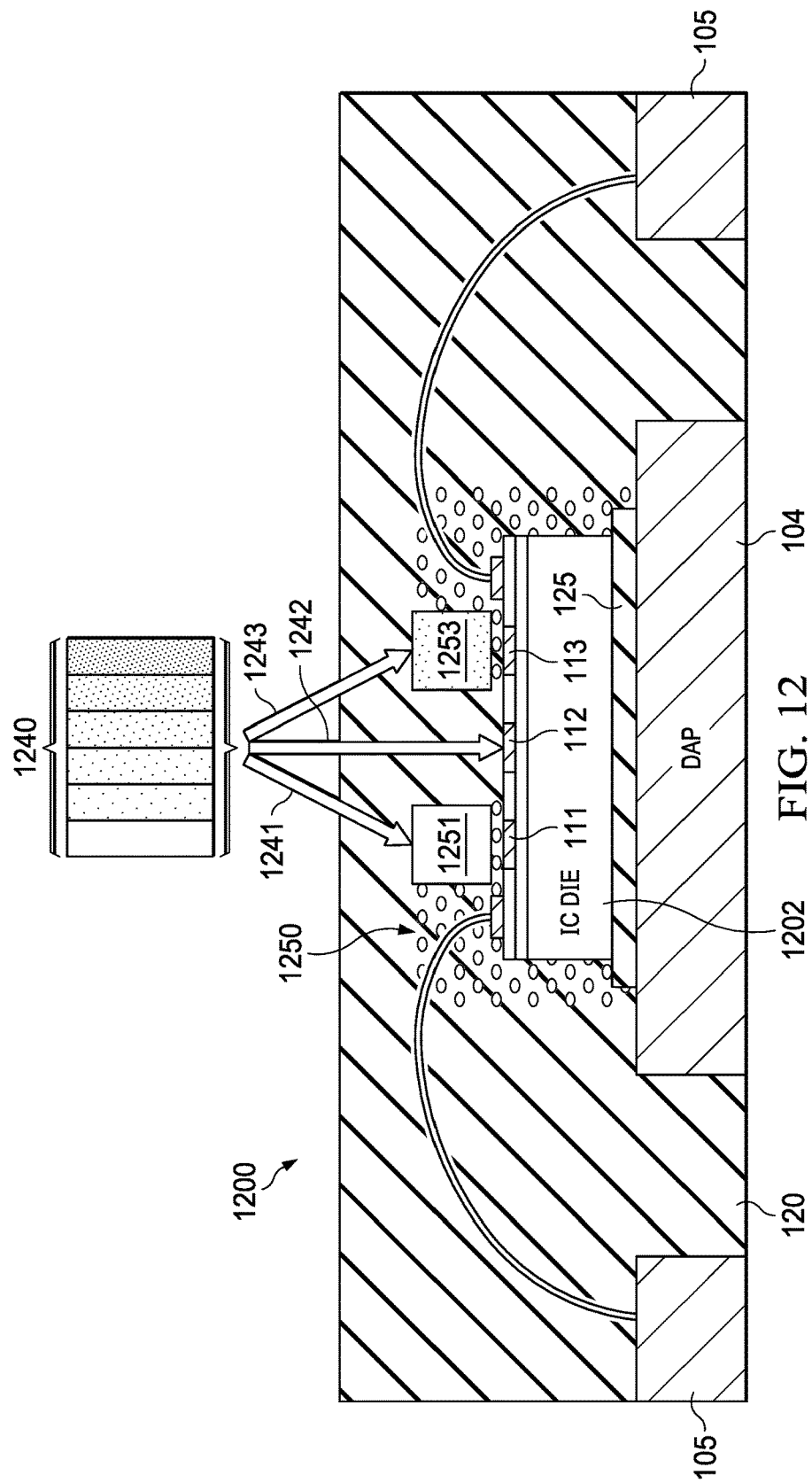

FIG. 12 is a cross sectional view of encapsulated package 1200 that includes an embodiment of a spectrometer that uses filter structure 1250 that is formed within the encapsulation material 120 by a PBG structure that includes PBG regions 1251 and 1253. PBG region 1251 may be designed to block a first frequency band, while PBG region 1253 may be designed to block a different second frequency band.

In this example, a broad spectrum electromagnetic signal 1240 is impinging on encapsulated package 1200. In this example, signal 1240 may be an optical signal or a radio frequency signal (RF) that is similar to signal 640 as shown in FIG. 6, for example. In this example, the spectrum of signal 1240 is illustrated as having six frequency bands each approximately equal in size to the bandgap provided by PBG regions 1251, 1253.

In this example, IC die 1202 includes three broad spectrum sensors 111-113 as shown in FIG. 6. IC die may be the same or similar as IC die 102 shown in FIG. 6. In this example, a photonic waveguide region is provided to allow signal portion 1242 of electromagnet signal 1240 to reach sensor 112. Similar portions 1241, 1243 of electromagnetic signal 1240 are provided to PBG regions 1251 and 1253. PBG region 1251 may block a first band of portion 1241 and PBG region 1253 may block a second band of portion 1243.

In this manner, a magnitude value may be measured by sensor 112 for broad spectrum signal 1240 as represented by portion 1242. A magnitude value may be measured by sensor 111 that indicates the magnitude of signal 1240 minus the first band of energy. Similarly, a magnitude value may be measured by sensor 113 that indicates the magnitude of signal 1240 minus the second band of energy. Processing circuitry on IC die 1202 or on another system coupled to IC die 1202 may then easily calculate a value for the magnitude of the first band and of the second band.

A different spectrometer may be provided by using the same IC die 1202, and forming PBG regions with different bandgap, or multiple bandgaps for filter structure 1250 during the encapsulation process. In this manner, several different devices may be fabricated to sense different bands by using a same type of IC die. Only the encapsulation process needs to be modified to change the spectral sensing parameters by selecting which bandgap to implement. In some embodiments, multiple bandgaps may be included in a PBG region to allow a sensor to sense energy for more than one band.

While three sensors are illustrated here for clarity, another embodiment may have a larger array of sensors to provide a spectrometer with more precision.

Figure 13:
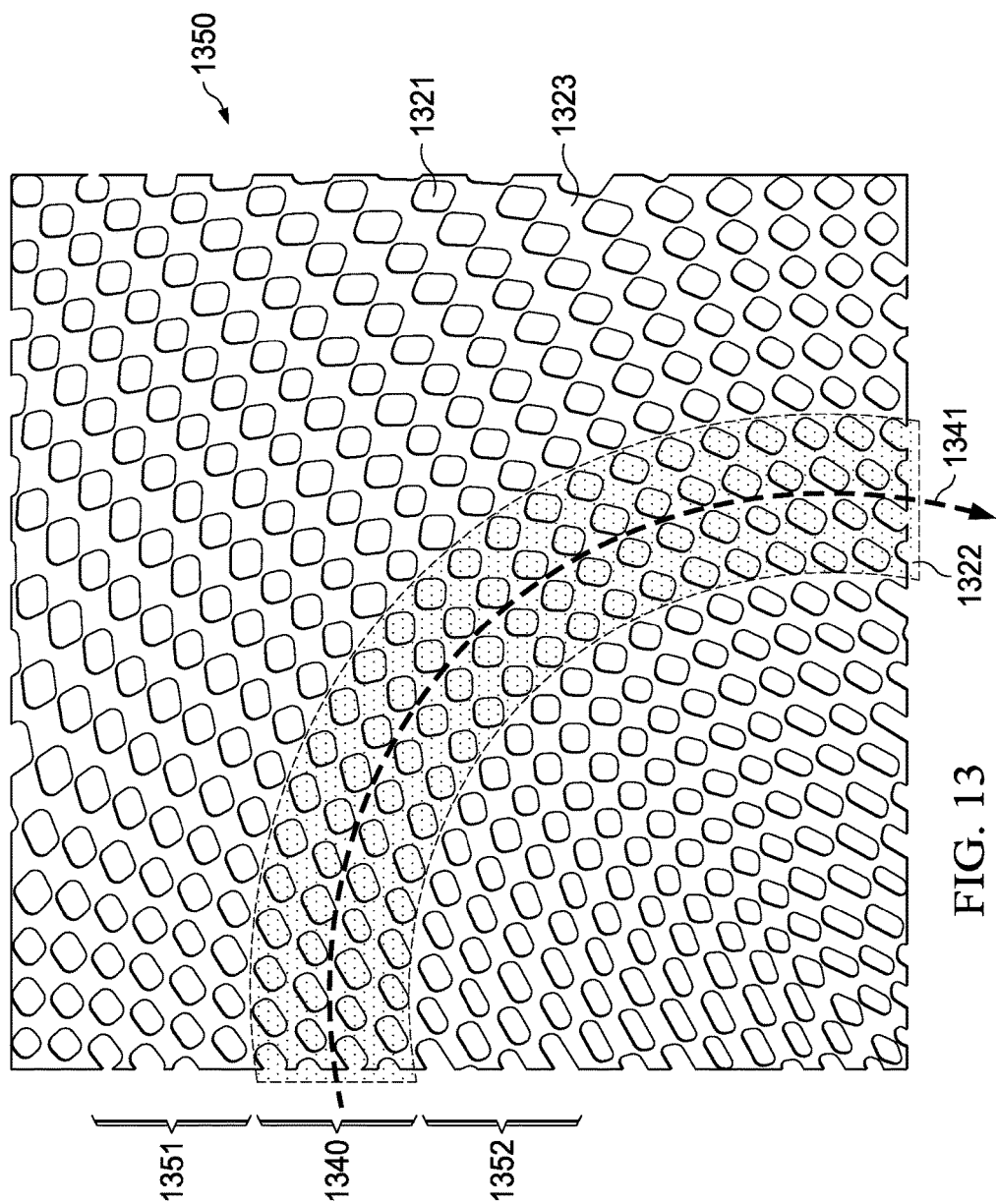
FIG. 13 illustrates a simulation of another example photonic waveguide.

FIG. 13 illustrates a simulation of another example photonic waveguide 1340 formed within a photonic structure 1350. Photonic structure 1350 is similar to photonic structure 550 as illustrated in FIG. 5 in that an array of nodes 1321 within a lattice material 1323 form an approximately periodic structure. However, in this example photonic waveguide region 1340 may be populated with nodes 1322. Nodes 1322 may be the same as nodes 1321, or they may be different in intrinsic properties, shape, spacing, etc.

In this example, a continuous lattice may be provided that steers the photon energy 1341 by curving the lattice in the direction of travel. The nodes 1322 in the "pathway" do not improve propagation but do steer it. In this manner, the space in the path of the photons may be warped as opposed to creating a hallway for them to bounce down. This may be analogous to a boat on a river; the river (curved lattice) is already flowing in a certain direction and pulls the boat (photon) in that direction.

An additive process as described above in more detail with reference to FIGS. 8A-8C may be used to place the array of nodes to form the curved lattice during encapsulation of an encapsulated package.

Nodes 1322 within photonic waveguide region 1340 may configured such that they do not provide a bandgap to the frequency of photonic signal 1341 so that photonic signal 1341 may propagate through photonic waveguide region 1340.

Nodes 1321 may also be configured such that they do not provide a bandgap to the frequency of photonic signal 1341. However, the photonic energy of photonic signal 1341 may be directed along photonic waveguide region by curving the lattice of photonic structure 1350 to maintain an approximately smooth wall of nodes 1321 along the edge of phonic waveguide region 1340. Similarly, nodes 1322 are arranged in a curved manner to provide a pathway for phonons 1341. Photonic structure 1350 may be referred to as a "resonant structure" that acts as a bandpass structure as opposed to a bandgap structure.

Figure 14:
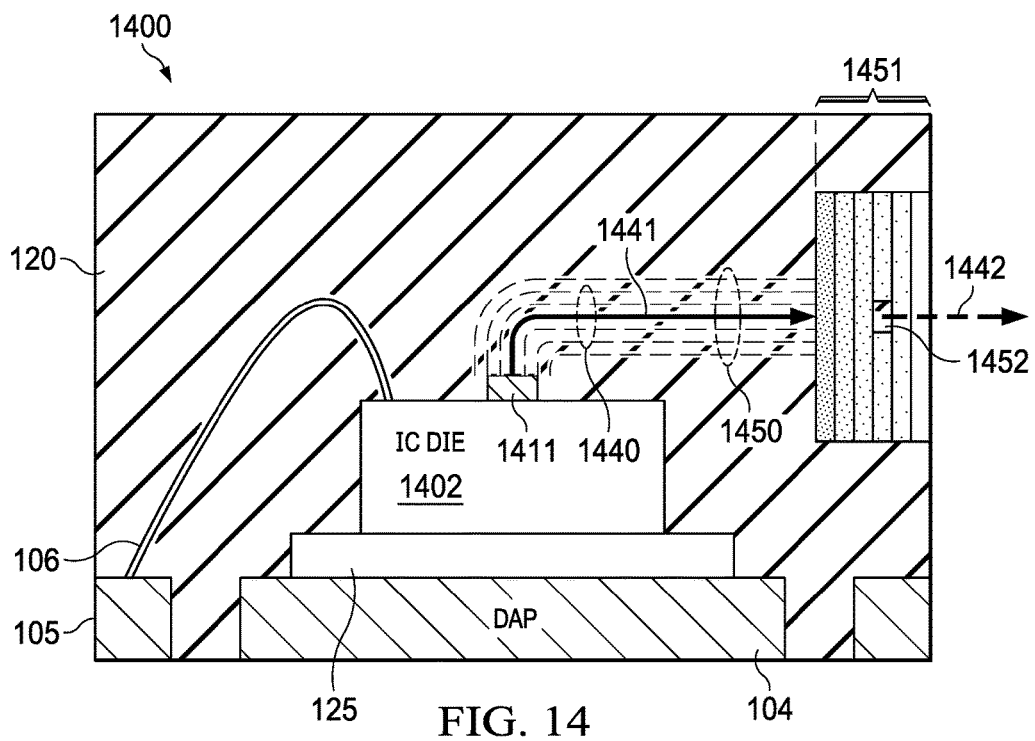
FIG. 14 is a cross sectional view of another example encapsulated package that includes a photonic waveguide formed by a resonant structure coupled to a filter structure.

FIG. 14 is a cross sectional view of another example encapsulated package 1400 that includes a photonic waveguide 1440 formed by a resonant structure 1450. In this example, resonant structure 1450 is implemented in a similar manner as resonant structure 1350 as shown in FIG. 13 and relies on warping the lattice structure to guide phonon stream 1441 from a transmitter on IC die 102 to a receiver on IC die 103.

As described in more detail above, a photonic filter structure 1452 may be included in the encapsulation material package 1400 that may be designed to pass only a certain band or range of frequencies out of or into a sensor or emitter 1411 located on IC die 1402. In this example, photonic filter structure 1451 is a multilayer filter structure that may be similar to filter structure 650 shown in FIG. 6. In other embodiments, other types of photonic filter structures may be included, such as waveguide structure 150 as shown in FIG. 1 or structure 1250 as shown in FIG. 12.

Figure 15:
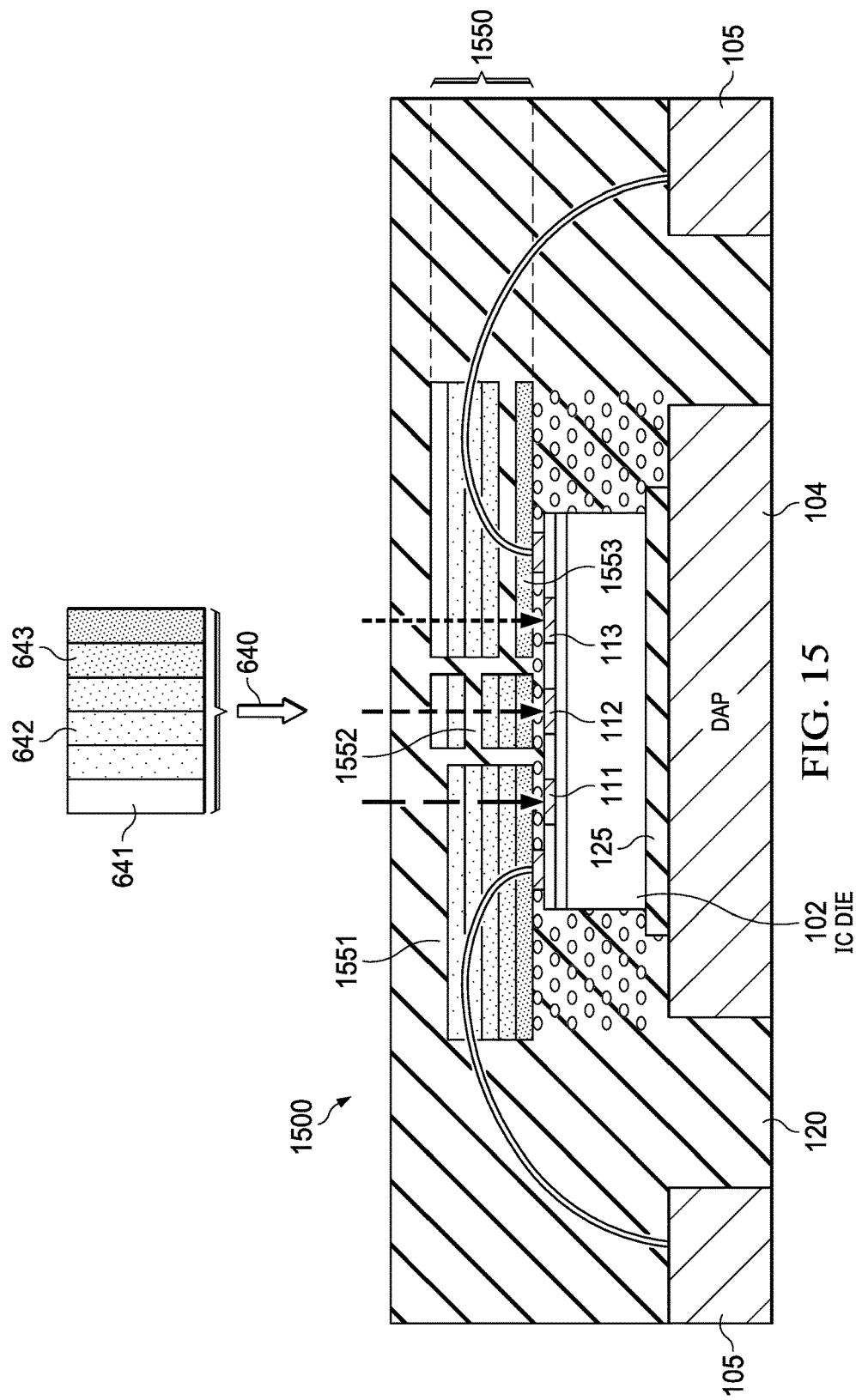
FIG. 15 is a cross sectional view of another example encapsulated package that includes a multilayer photonic filter structure.

FIG. 15 is a cross sectional view of another example encapsulated package 1500 that includes a multilayer photonic filter structure 1550. This example may be similar to multilayer photonic structure 650 as shown in FIG. 6, except that in this case one or more layers of the multilayer filter structure may be omitted in some portions of the filter structure.

In this example, a broadband electromagnetic signal 640 is impinging on encapsulated package 1500. In this example, signal 640 may be an optical signal or a radio frequency signal (RF), for example. For illustrative purposes only, signal 640 is illustrated as having a spectrum of six frequency bands, such as band 641, 642, 643, to correspond to the six bandgaps provided by the six layer filter structure 1550. Signal 640 may have a broader spectrum or a narrower spectrum than what is included in multilayer filter structure 1550, for example.

Assuming the bandgap of each of the six layers of filter structure 1550 is designed cover a different portion of the spectrum and all six together can block the entire spectrum, then no portion of signal 640 would reach any of sensors 111-113. However, in this example, a one or more layers of bandgap material may be omitted in selected portions of filter structure 1550 to allow energy in a selected band to flow through filter structure 1550. For example, a layer 1551 may be omitted from filter structure 1550 to allow frequencies in a selected band, such as the band indicated at 641, to flow through the filter structure and be sensed by sensor 111. Another layer region 1552 may be omitted in another portion of filter structure 1550 to allow frequencies in another selected band, such as the band indicated at 642, to flow through the filter structure and be sensed by sensor 112. Similarly, layer 1553 region 1553 may be omitted in another portion of filter structure 1550 to allow frequencies in another selected band, such as the band indicated at 643, to flow through the filter structure and be sensed by sensor 113. In this example, a spectrometer may be provided that may sense energy in three different energy bands in signal 640.

A different spectrometer may be provided by using the same IC die 102, and omitting different layers of filter structure 1550 during the encapsulation process. In this manner, several different devices may be fabricated to sense different bands by using a same type of IC die. Only the encapsulation process needs to be modified to change the spectral sensing parameters by selecting which layers to omit. In some embodiments, several layers may be omitted to allow a sensor to sense energy for more than one band.

While three sensors are illustrated here for clarity, another embodiment may have a larger array of sensors to provide a spectrometer with more precision.

While a filter structure 1550 is illustrated herein that has approximately contiguous bandgaps, another embodiment may use a filter structure in which the bandgaps are not contiguous. In that case, electromagnetic energy that is not blocked by any bandgap in the bandgap structure may be sensed by an underlying sensor.

In some embodiments, a separate portion of the filter over each sensor may be tailored to have no bandgap in the frequency range intended to be sensed by each sensor.

Other Embodiments

While the disclosure has been described with reference to illustrative embodiments, this description is not intended to be construed in a limiting sense. Various other embodiments of the disclosure will be apparent to persons skilled in the art upon reference to this description. For example, in some embodiments, the lattice material may have a relatively low dielectric constant value and the node material may have relatively high dielectric constant value. In other embodiments, the lattice material may have relatively high dielectric constant value and the node material may have a relatively low dielectric constant value. In some embodiments, the node material may be air, another gas, or a vacuum, for example.

While photonic structures using materials with different permittivities were described herein, other embodiments may use materials having differences in other intrinsic properties, such as permeability, conductivity, etc.

In some embodiments, a portion of the nodes may be formed with one kind of material, while another portion of the nodes may be formed with a different material. Several different types of material may be used to form different sets of nodes within the photonic bandgap structure to thereby tailor the performance of the photonic bandgap structure.

In some embodiments, a portion of the nodes may be formed with one lattice constant, while another portion of the nodes may be formed with a different lattice constant. Several different lattice constants may be used to form different sets of nodes within the photonic bandgap structure to thereby tailor the performance of the photonic bandgap structure The nodes may be fabricated using various materials, such as: various polymers such as polyurethane, polyacrylates, etc., ceramic materials, metals, gases such as natural air, nitrogen etc. In some cases, a vacuum may be left and therefore no material would be used for some lattice nodes.

In some embodiments, the photonic structure may be symmetric in 3D, while in other embodiments the photonic structure may be asymmetric with different lattice spacing in different directions.

In some embodiments, the photonic structure may have a bandgap that is effective in all directions, while in other embodiments the photonic structure may have a bandgap in one direction but not in another direction, for example.

in another embodiment, an IC die may be partially or completely surrounded by a photonic bandgap structure in the form of an enclosure that surrounds the IC, such as a box shaped or spherical shaped enclosure that is formed within the encapsulation material by selective placement of nodes within the encapsulation material.

Another embodiment may include packages that are entirely encased in mold compound, such as a dual inline package (DIP).

In another embodiment, the PBG structure may be made with ferroelectric or magnetic material. In this case, a field bias may be applied to the PBG structure using coils or plates located on the IC die or adjacent to the IC die to tune the bandgap. The amount of bias may be controlled by control circuitry located on the IC die, or by control circuitry that is external to the IC die.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the disclosure should not be considered limited to the specific ordering of steps shown in the figures and/or described herein.

It is therefore contemplated that the appended claims will cover any such modifications of the embodiments as fall within the true scope and spirit of the disclosure.

What is claimed is:

1. A An encapsulated package comprising:
   an integrated circuit (IC) die;
   sensors the IC die, the sensors configured to receive electromagnetic energy and to generate signals in response to the electromagnetic energy;
   a filter structure including: a first region configured to pass a first band of the electromagnetic energy to the sensors or to block the first band of the electromagnetic energy from passing to the sensors; and a second region configured to pass a second band of the electromagnetic energy to the sensors or to block the second band of the electromagnetic energy from passing to the sensors; and
   an encapsulation material encapsulating the IC die, the sensors and the filter structure, in which the filter structure includes a diffusion of particles within the encapsulation material, the encapsulation material having a first intrinsic property, and the particles having a second intrinsic property that is different from the first intrinsic property.

2. A package comprising:
   an integrated circuit (IC) die;
   sensors on the IC die, the sensors configured to receive electromagnetic energy and to generate signals in response to the electromagnetic energy;
   a filter structure including: a first region configured to pass a first band of the electromagnetic energy to the sensors or to block the first band of the electromagnetic energy from passing to the sensors; and a second region configured to pass a second band of the electromagnetic energy to the sensors or to block the second band of the electromagnetic energy from passing to the sensors; and
   an encapsulation material encapsulating the IC die, the sensors and the filter structure;
   in which the filter structure is a photonic wave collimating structure or a multilayer photonic bandgap structure.

3. The package of claim 1, in which the filter structure is a photonic wave collimating structure or a multilayer photonic bandgap structure.

4. The package of claim 1, in which the filter structure: has an open path for a particular band of the electromagnetic energy to pass to a first one of the sensors; and is configured to block the particular band of the electromagnetic energy from passing to a second one of the sensors.

5. The package of claim 1, in which the filter structure includes a matrix of periodically spaced nodes within the encapsulation material, the encapsulation material having the first intrinsic property, and the nodes having the second intrinsic property.

6. The package of claim 1, in which the filter structure is a photonic resonant structure.

7. The package of claim 2, in which the filter structure includes a diffusion of particles within the encapsulation material, the encapsulation material having a first intrinsic property, and the particles having a second intrinsic property that is different from the first intrinsic property.

8. A package comprising:
   an integrated circuit (IC) die;
   an emitter on the IC die, the emitter configured to emit electromagnetic energy;
   a filter structure configured to pass a first band of the electromagnetic energy emitted by the emitter while blocking a second band of the electromagnetic energy emitted by the emitter; and
   an encapsulation material encapsulating the IC die, the emitter and the filter structure, in which the filter structure includes a diffusion of particles within the encapsulation material, the encapsulation material having a first intrinsic property, and the particles having a second intrinsic property that is different from the first intrinsic property.

9. A package comprising:
   an integrated circuit (IC) die;
   an emitter on the IC die, the emitter configured to emit electromagnetic energy;
   a filter structure configured to pass a first band of the electromagnetic energy emitted by the emitter while blocking a second band of the electromagnetic energy emitted by the emitter; and
   an encapsulation material encapsulating the IC die, the emitter and the filter structure;
   in which the filter structure is a photonic wave collimating structure or a multilayer photonic bandgap structure.

10. The package of claim 8, in which the photonic filter structure is a photonic wave collimating structure or a multilayer photonic bandgap structure.

11. The package of claim 8, in which the photonic filter structure includes a matrix of periodically spaced nodes within the encapsulation material, the encapsulation material having the first intrinsic property, and the nodes having have the second intrinsic property.

12. The encapsulated package of claim 9, in which the photonic filter structure includes a diffusion of particles within the encapsulation material, wherein the encapsulation material having has-a first intrinsic property and the particles having nodes have a second intrinsic property that is different from the first intrinsic property.

13. The package of claim 8, further comprising a photonic resonant structure between the emitter and the filter structure.

14. The package of claim 2, in which the filter structure: has an open path for a particular band of the electromagnetic energy to pass to a first one of the sensors; and is configured to block the particular band of the electromagnetic energy from passing to a second one of the sensors.

15. The package of claim 2, in which the filter structure includes a matrix of periodically spaced nodes within the encapsulation material, the encapsulation material having a first intrinsic property, and the nodes having a second intrinsic property that is different from the first intrinsic property.

16. The package of claim 2, in which the filter structure is a photonic resonant structure.

17. The package of claim 9, in which the filter structure includes a matrix of periodically spaced nodes within the encapsulation material, the encapsulation material having a first intrinsic property, and the nodes having a second intrinsic property that is different from the first intrinsic property.

18. The package of claim 9, further comprising a photonic resonant structure between the emitter and the filter structure.

\* \* \* \* \*